US008809050B2

(12) United States Patent
Vera et al.

(10) Patent No.: US 8,809,050 B2
(45) Date of Patent: Aug. 19, 2014

(54) METHODS OF CELL CULTURE FOR ADOPTIVE CELL THERAPY

(75) Inventors: Juan F. Vera, Bellaire, TX (US); Cliona M Rooney, Bellaire, TX (US); Ann M. Leen, Bellaire, TX (US); John R. Wilson, New Brighton, MN (US)

(73) Assignee: Wilson Wolf Manufacturing, New Brighton, MN (US)

( * ) Notice: Subject to any disclaimer, the term of this patent is extended or adjusted under 35 U.S.C. 154(b) by 200 days.

(21) Appl. No.: 12/963,597

(22) Filed: Dec. 8, 2010

(65) Prior Publication Data

US 2011/0136228 A1 Jun. 9, 2011

Related U.S. Application Data

(60) Provisional application No. 61/267,761, filed on Dec. 8, 2009.

(51) Int. Cl.
*C12N 5/00* (2006.01)

(52) U.S. Cl.
USPC ........................................................ 435/325

(58) Field of Classification Search
None
See application file for complete search history.

(56) References Cited

U.S. PATENT DOCUMENTS

| | | | |
|---|---|---|---|
| 4,649,118 | A | 3/1987 | Anderson |
| 5,248,769 | A | 9/1993 | Dorin |
| 5,585,266 | A | 12/1996 | Plitt et al. |
| 5,707,869 | A | 1/1998 | Wolf et al. |
| 5,731,160 | A | 3/1998 | Melief et al. |
| 5,962,318 | A | 10/1999 | Rooney et al. |
| 2003/0235908 | A1 | 12/2003 | Berenson et al. |
| 2005/0106717 | A1 | 5/2005 | Wilson et al. |
| 2005/0227354 | A1* | 10/2005 | Sagawa et al. .............. 435/372 |
| 2009/0111180 | A1 | 4/2009 | Vilendrer et al. |
| 2010/0261269 | A1 | 10/2010 | June et al. |
| 2011/0129923 | A1 | 6/2011 | Wilson et al. |
| 2011/0136228 | A1 | 6/2011 | Vera et al. |
| 2011/0287542 | A1 | 11/2011 | Wilson et al. |
| 2011/0287543 | A1 | 11/2011 | Wilson et al. |

FOREIGN PATENT DOCUMENTS

| | | |
|---|---|---|
| EP | 2119778 A1 | 11/2009 |
| JP | 10-174581 | 6/1998 |
| WO | WO 2004/106484 | 12/2004 |
| WO | WO 2005/047466 | 5/2005 |
| WO | WO 2006/026746 | 3/2006 |

OTHER PUBLICATIONS

Application and File History of U.S. Appl. No. 10/961,814, Inventors Wilson et al., filed Oct. 8, 2004.
Application and File History of U.S. Appl. No. 13/029,762, Inventors Wilson et al., filed Feb. 17, 2011.
Application and File History of U.S. Appl. No. 13/194,298, Inventors Wilson et al., filed Jul. 29, 2011.
Application and File History of U.S. Appl. No. 13/194,363, Inventors Wilson et al., filed Jul. 29, 2011.
International Search Report and Written Opinion for PCT/US2010/059591, Applicant Wilson Wolf Manufacturing Corporation et al., dated Aug. 22, 2011 (6 pgs).
Nakazawa et al., "Optimization of the PiggyBac Transposon System for the Sustained Genetic Modification of Human T Lymphocytes," J. Immunother., 2009, vol. 32, No. 8, pp. 826-836.
Vera et al., "Accelerated Production of Antigen-specific T Cells for Preclinical and Clinical Applications Using Gas-permeable Rapid Expansion Cultureware (G-Rex)," J. Immunother. 2009, vol. 00, No. 00, pp. 1-11.
Vera et al., "Immunotherapy of Human Cancers Using Gene Modified T Lymphocytes," Curr. Gene Ther., Oct. 2009, vol. 9, No. 5, pp. 396-408.
Gerdemann, Ulrike, et al. "Generation of Multivirus-specific T Cells to Prevent/treat Viral Infections after Allogeneic Hematopoietic Stem Cell Transplant". Journal of Visualized Experiments, May 27, 2011, vol. 51, e. 2736 (pp. 1-6).
International Search Report and Written Opinon for PCT Application PCT/US2013/045209, dated Sep. 25, 2013, 5 pgs.
International Search Report for PCT Application PCT/US2013/041861, dated Aug. 23, 2013, 5 pgs.
Extended European Search Report from related European Application No. 13192463.1-1403/2698430, dated Feb. 4, 2014, 8 pgs.
Extended European Search Report from related European Application No. 10836660.0-2510086, Apr. 24, 2013, 7 pgs.
International Preliminary Report on Patentability from related PCT Application PCT/US2010/059591, dated Jun. 21, 2012, 2 pgs.
Brenner, L., et al. "Rapid Generation of Antigen-Specific T Cells for Pre-Clinical and Clinical Applications Using a novel Mini Cell Bioreactor", Biology of Blood and Marrow Transplantation, vol. 15, No. 2, Feb. 1, 2009, p. 137.
Hoffmann, Petra, et al. "Large-scale in vitro expansion of polyclonal human CD4+CD5 high regulatory T cells", Blood, vol. 104, No. 3, Aug. 1, 2004, pp. 895-903.
Papanicolaou, G.A., et al. "Rapid expansion of cytomegalovirus-specific cytotoxic T lymphocytes by artificial antigen-presenting cells expressing a single HLA allele", Blood, vol. 102, No. 7, Oct. 1, 2003, pp. 2498-2505.
Office Action dated Dec. 18, 2013 from related U.S. Appl. No. 13/493,768, 10 pgs.

* cited by examiner

*Primary Examiner* — Suzanne M Noakes
*Assistant Examiner* — Stephen Chong
(74) *Attorney, Agent, or Firm* — Patterson Thuente Pedersen, P.A.

(57) ABSTRACT

An improved method of culturing cells for cell therapy applications that includes growing desired cells in the presence of antigen-presenting cells and/or feeder cells and with medium volume to surface area ratio of up to 1 ml/cm$^2$ if the growth surface is not comprised of gas permeable material and up to 2 ml/cm$^2$ if the growth surface is comprised of gas permeable material. The desired cells are at a surface density of less than $0.5 \times 10^6$ cells/cm$^2$ at the onset of a production cycle, and the surface density of the desired cells plus the surface density of the antigen presenting cells and/or feeder cells are at least about $1.25 \times 10^5$ cells/cm$^2$.

14 Claims, 16 Drawing Sheets

Fig. 2

| EXPECTED AND OBSERVED CTL EXPANSION | | | | | | | |
|---|---|---|---|---|---|---|---|
| CELL DOUBLING | 1 | 2 | 3 | 4 | 5 | 6 | 7 |
| EXPECTED FOLD EXPANSION | 2 | 4 | 8 | 16 | 32 | 64 | 128 |
| OBSERVED FOLD EXPANSION (DAY 0 TO 9) | | | | | | | 258 RANGE (48 TO 409) |
| OBSERVED FOLD EXPANSION (DAY 9 TO 16) | | | | | | | 5.7 RANGE (2.2 TO 10.6) |
| OBSERVED FOLD EXPANSION (DAY 16 TO 23) | | | | | | | 4.3 RANGE (4.1 TO 14.9) |

Fig. 15

| | CONVENTIONAL | | | | |
|---|---|---|---|---|---|
| CYCLE | 1 | 2 | 3 | 4 | 5 |
| DAYS PER CYCLE | 7 | 7 | 7 | 7 | 7 |
| CUMULATIVE DAYS | 7 | 14 | 21 | 28 | 35 |
| SURFACE AREA (CM²) | 4 | 16 | 64 | 256 | 1024 |
| STARTING SURFACE DENSITY (CELLS/CM²) | 1 | 1 | 1 | 1 | 1 |
| FINAL SURFACE DENSITY (CELLS/CM²) | 2 | 2 | 2 | 2 | 2 |
| CELLS PRODUCED (x10⁶) | 8 | 32 | 128 | 512 | 2048 |

| | NOVEL | | |
|---|---|---|---|
| CYCLE | 1 | 2 | 3 |
| DAYS PER CYCLE (APPROX.) | 9.5 | 9.5 | 15.0 |
| CUMULATIVE DAYS | 9.5 | 19.0 | 34.0 |
| SURFACE AREA (CM²) | 8 | 625 | 46875 |
| STARTING SURFACE DENSITY (CELLS/CM²) | 0.06 | 0.06 | 0.06 |
| FINAL SURFACE DENSITY (CELLS/CM²) | 4.50 | 4.50 | 4.50 |
| CELLS PRODUCED (x10⁶) | 38 | 2813 | 210938 |

Fig. 16

| | | CONVENTIONAL | | | | |
|---|---|---|---|---|---|---|
| CYCLE | 1 | 2 | 3 | 4 | 5 | |
| DAYS PER CYCLE | 7 | 7 | 7 | 7 | 7 | |
| CUMULATIVE DAYS | 7 | 14 | 21 | 28 | 35 | |
| SURFACE AREA (CM$^2$) | 4 | 16 | 64 | 256 | 1024 | |
| STARTING SURFACE DENSITY (CELLS/CM$^2$) | 1 | 1 | 1 | 1 | 1 | |
| FINAL SURFACE DENSITY (CELLS/CM$^2$) | 2 | 2 | 2 | 2 | 2 | |
| CELLS PRODUCED (x10$^6$) | 8 | 32 | 128 | 512 | 2048 | |
| | | NOVEL | | | | |
| CYCLE | 1 | 2 | 3 | | | |
| DAYS PER CYCLE (APPROX.) | 9.5 | 9.5 | 15.0 | | | |
| CUMULATIVE DAYS | 9.5 | 19.0 | 34.0 | | | |
| SURFACE AREA (CM$^2$) | 8 | 625 | 4018 | | | |
| STARTING SURFACE DENSITY (CELLS/CM$^2$) | 0.06 | 0.06 | 0.70 | | | |
| FINAL SURFACE DENSITY (CELLS/CM$^2$) | 4.50 | 4.50 | 7.50 | | | |
| CELLS PRODUCED (x10$^6$) | 38 | 2813 | 30134 | | | |

METHODS OF CELL CULTURE FOR ADOPTIVE CELL THERAPY

RELATED APPLICATION

The present application claims the benefit of U.S. Provisional Application No. 61/267,761, filed Dec. 8, 2009, entitled "IMPROVED METHODS OF CELL CULTURE FOR ADOPTIVE CELL THERAPY", which is incorporated herein in its entirety by reference.

FIELD OF THE INVENTION

The present invention relates generally to methods of culturing cells, and more specifically to culturing cells for cell therapy.

BACKGROUND

Cell culture is major contributor to the cost and complexity of cell therapy. With current methods, the process of culturing the cells is time consuming and expensive. Typically, to produce a large number of cells, an in vitro culture process is undertaken that proceeds in stages. At the earliest stage, the desired cells are a relatively small population within a composition of cells that are placed into cell culture devices. In this stage, the composition of cells typically includes the source of the desired cells (such as peripheral blood mononuclear cells), feeder cells that stimulate growth of the desired cells, and/or antigen presenting. Culture devices and methods that allow the medium that cells reside in to be in a generally undisturbed state are favored since the cells remain relatively undisturbed. Such devices include standard tissue culture plates, flasks, and bags. The culture progresses in stages generally consisting of allowing the cell composition to deplete the medium of growth substrates such as glucose, removing the spent medium, replacing the spent medium with fresh medium, and repeating the process until the desired quantity of desired cells is obtained. Often, the cell composition is moved to other devices to initiate a new stage of production as the desired cell population increases and additional growth surface is needed. However, with conventional methods, the rate of population growth of the desired cells slows as the population of cells upon the growth surface increases. The end result is that it is very time consuming and complicated to produce a sizable population of desired cells.

State of the art production methods for generating T lymphocytes with antigen specificity to Epstein Barr virus (EBV-CTLs) provide an example of production complexity. The conventional method for optimal expansion of EBV-CTLs uses standard 24-well tissue culture plates, each well having 2 cm$^2$ of surface area for cells to reside upon and the medium volume restricted to 1 ml/cm$^2$ due to gas transfer requirements. The culture process begins by placing a cell composition comprised of PBMC (peripheral blood mononuclear cells) in the presence of an irradiated antigen presenting cell line, which may be a lymphoblastoid cell line (LCL), at a surface density (i.e. cells/cm$^2$ of growth surface) ratio of about 40:1 with about 1×10$^6$ PBMC/cm$^2$ and 2.5×10$^4$ irradiated antigen presenting cells/cm$^2$. That instigates the population of EBV-CTLs within the cell composition to expand in quantity. After 9 days, EBV-CTLs are selectively expanded again in the presence of irradiated antigen presenting LCL at a new surface density ratio of 4:1, with a minimum surface density of about 2.5×10$^5$ EBV-CTL/cm$^2$. Medium volume is limited to a maximum ratio of 1 ml/cm$^2$ of growth surface area to allow oxygen to reach the cells, which limits growth solutes such as glucose. As a result, the maximum surface density that can be achieved is about 2×10$^6$ EBV-CTL/cm$^2$. Thus, the maximum weekly cell expansion is about 8-fold (i.e. 2×10$^6$ EBV-CTL/cm$^2$ divided by 2.5×10$^5$ EBV-CTL/cm$^2$) or less. Continued expansion of EBV-CTLs requires weekly transfer of the EBV-CTLs to additional 24-well plates with antigenic re-stimulation, and twice weekly exchanges of medium and growth factors within each well of the 24-well plate. Because conventional methods cause the rate of EBV-CTL population expansion to slow as EBV-CTL surface density approaches the maximum amount possible per well, these manipulations must be repeated over a long production period, often as long as 4-8 weeks, to obtain a sufficient quantity of EBV-CTLs for cell infusions and quality control measures such as sterility, identity, and potency assays.

The culture of EBV-CTLs is but one example of the complex cell production processes inherent to cell therapy. A more practical way of culturing cells for cell therapy that can reduce production time and simultaneously reduce production cost and complexity is needed.

We have created novel methods that increase the population growth rate throughout production, and by so doing, reduce the complexity and time needed to produce cells.

SUMMARY

It has been discovered that the production of cells for cell therapy can occur in a shorter time period and in a more economical manner than is currently possible by using a staged production process that allows unconventional conditions to periodically be re-established throughout the production process. The unconventional conditions include reduced surface density (i.e. cells/cm$^2$) of desired cells, novel ratios of desired cells to antigen presenting and/or feeder cells, and/or use of growth surfaces comprised of gas permeable material with increased medium volume to surface area ratios.

Embodiments of this invention relate to improved methods of culturing cells for cell therapy applications. They include methods that reduce the time, cost, and complexity needed to generate a desired number of desired cells by use of various novel methods that allow the desired cell population to maintain a higher growth rate throughout the production process relative to conventional methods.

One aspect of the present invention relies on conducting the culture process in stages and establishing conditions at the onset of one or more stages that allow the growth rate of the desired cell population to exceed what is currently possible. At least one stage of culture, and preferably nearly all, establish initial conditions that include the desired cells resting either on non-gas permeable or gas permeable growth surfaces at unconventionally low surface density and at an unconventional ratio of antigen presenting cells (and/or feeder cells) per desired cell. By using the novel embodiments of this aspect of the invention, the desired cell population can experience more doublings in a shorter period of time than allowed by conventional methods, thereby reducing the duration of production.

Another aspect of the present invention relies on conducting the culture process in stages and establishing conditions at the onset of one or more stages such that the growth rate of the desired cell population exceeds what is currently possible. At least one stage of culture, and preferably nearly all, establish conditions that include the desired cells resting on a growth surface comprised of gas permeable material at unconventionally high medium volume to growth surface area ratios. By using the novel embodiments of this aspect of the invention, the desired cell population can experience more doublings in a shorter period of time than is allowed by conventional methods, thereby reducing the duration of production.

Another aspect of the present invention relies on conducting the culture process in stages and establishing conditions of each stage such that the growth rate of the desired cell population exceeds what is currently possible. At least one stage of culture, and preferably nearly all, establish initial conditions that include the desired cells resting on growth surfaces comprised of gas permeable material at unconventionally low surface density (i.e. cells/cm$^2$) with an unconventional ratio of antigen presenting cells (and/or feeder cells) per desired cell and in the presence of unconventionally high medium volume to growth surface area ratios. By using the novel embodiments of this aspect of the invention, the desired cell population can experience more doublings in a shorter period of time than conventional methods allow, thereby reducing the duration of production.

BRIEF DESCRIPTION OF THE DRAWINGS

The invention may be more completely understood in consideration of the following detailed description of various embodiments of the invention in connection with the accompanying drawings, in which:

FIG. 2 shows a table that illustrates the discrepancy between the potential expansion and observed fold expansion of antigen-specific T-cells in Example 1.

FIG. 15 shows a comparison of each production method depicted in FIG. 14 to demonstrate the power of the novel method and why it is useful to adjust the production protocol at various stages to fully capture the efficiency.

FIG. 16 shows an example of how one could adjust the production protocol in the novel method to gain efficiency as production progresses.

DETAILED DESCRIPTION

Definitions

Figure 1:
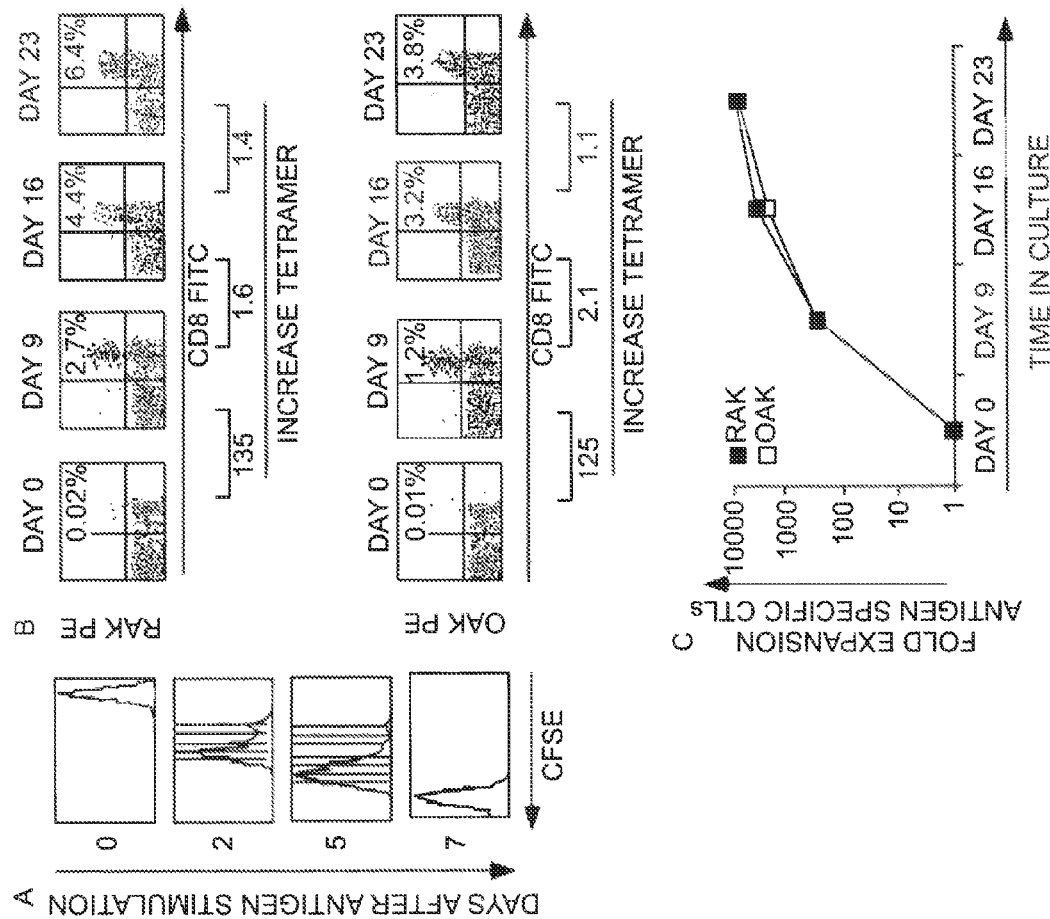
FIG. 1A shows the population of antigen-specific T-cells in Example 1 undergoes at least 7 cell doublings after the initial stimulation over the first 7 days.
FIG. 1B shows data demonstrating the magnitude of expansion of a T-cell population within a cell composition over time as determined by tetramer analysis for Example 1.
FIG. 1C the rate of population growth of antigen-specific T-cells diminishes over a 23 day period in Example 1.

Antigen presenting cells (APC): Cells that act to trigger the desired cells to respond to a particular antigen.

CTL: Cytotoxic T cell

Desired cells: The specific type of cell that that the production process aims to expand in quantity. Generally the desired cells are non-adherent and examples includie regulatory T cells (Treg), natural killer cells (NK), tumor infiltrating lymphocytes (TIL), primary T lymphocytes and a wide variety of antigen specific cells, and many others (all of which can also be genetically modified to improve their function, in-vivo persistence or safety). Cells required for clinical use can be expanded with feeder cells and/or antigen presenting cells that can include PBMC, PHA blast, OKT3 T, B blast, LCLs and K562, (natural or genetically modified to express and antigen and/or epitope as well as co-stimulatory molecules such as 41BBL, OX40, CD80, CD86, HLA, and many others) which may or may not be pulsed with peptide or other relevant antigens.

EBV: Epstein Barr Virus

EBV-CTL: A T-cell that specifically recognized EBV-infected cells or cells expressing or presenting EBV-derived peptides through its T cell surface receptor.

EBV-LCL: Epstein Barr virus transformed B lymphoblastoid cell line.

Feeder cells: Cells that act to cause the desired cells to expand in quantity. Antigen presenting cells can also act as feeder cells in some circumstances.

Growth surface: The area within a culture device upon which cells rest.

PBMCs: Peripheral Blood Mononuclear Cells derived from peripheral blood, which are a source of some of the desired cells and which can act as feeder cells.

Responder (R): A cell that will react to a stimulator cell.

Static cell culture: A method of culturing cells in medium that is not stirred or mixed except for occasions when the culture device is moved from location to location for routine handling and/or when cells are periodically fed with fresh medium and the like. In general, medium in static culture is typically in a quiescent state. This invention is directed to static cell culture methods.

Stimulated: The effect that antigen presenting and/or feeder cells have on the desired cells.

Stimulator (S): A cell that will influence a responder cell.

Surface density: The quantity of cells per unit area of the surface within the device upon which the cells rest.

In attempting to find novel methods to simplify the production of a desired population of cells for adoptive T cell therapy, a series of experiments were conducted that have that opened the door to more efficient culture of cells for cell therapy applications. Numerous illustrative examples and various aspects of the present invention are described to indicate how the ability to reduce production time and complexity relative to conventional methods can be achieved.

EXAMPLE 1

Demonstration of Limitations of Conventional Methods

The data of this example demonstrate the limits of conventional culture methods for the production of EBV-CTL in standard 24 well tissue culture plates (i.e. 2 $cm^2$ surface area per well) using a medium volume of 2 ml per well (i.e. medium height at 1.0 cm and a medium volume to surface area ratio of 1 $ml/cm^2$).

Stage 1 of culture, day 0: The expansion of an EBV-CTL population was initiated by culturing a cell composition of PBMCs from normal donors (about $1\times10^6$ cells/ml) with antigen presenting gamma-irradiated (40 Gy) autologous EBV-LCLs at a 40:1 ratio (PBMC:LCLs) and a medium volume to growth surface ratio of 1 $ml/cm^2$ thereby establishing a cell composition surface density of about $1\times10^6$ cells/$cm^2$ in RPMI 1640 supplemented with 45% Click medium (Irvine Scientific, Santa Ana, Calif.), with 2 mM GlutaMAX-I, and 10% FBS.

Stage 2 of culture, day 9-16: On day 9, EBV-CTLs were harvested from the cell composition created in Stage 1, resuspended in fresh medium at a surface density of $0.5\times10^6$ EBV-CTL/$cm^2$ and re-stimulated with irradiated autologous EBV-LCLs at a ratio 4:1 CTL:LCL (surface density $0.5\times10^6$ CTL/$cm^2$:$1.25\times10^5$ LCL/$cm^2$). On day 13, 1 ml of the 2 ml medium volume in each well of the 24-well plates was removed and replaced with 1 ml of fresh medium containing recombinant human IL-2 (IL-2) (50 U/mL) (Proleukin; Chiron, Emeryville, Calif.).

Stage 3 of culture, day 17-23: The conditions of Stage 2 were repeated with twice weekly addition of IL-2 and the culture was terminated on day 23. Although the culture was terminated, it could have been continued with additional culture stages that mimicked that of stages 2 and 3.

Cell lines and tumor cells for use as target cells in Cytotoxicity assays: BJAB (a B cell lymphoma) and K562 (a chronic erythroid leukemia) were obtained from the American Type Culture Collection (ATCC, Rockville, Md., USA). All cells were maintained in culture with RPMI 1640 medium (GIBCO-BRL, Gaithersburg, Md.) containing 10% heat-inactivated fetal calf serum (FCS), 2 mM L-glutamine, 25 IU/mL penicillin, and 25 mg/mL streptomycin (all from BioWhittaker, Walkersville, Md.). Cells were maintained in a humidified atmosphere containing 5% $CO_2$ at 37° C.

Immunophenotyping:

Cell surface: Cells were stained with Phycoerythrin (PE), fluorescein isothiocyanate (FITC), periodin chlorophyll protein (PerCP) and allophycocyanin (APC)-conjugated monoclonal antibodies (MAbs) to CD3, CD4, CD8, CD56, CD16, CD62L, CD45RO, CD45RA, CD27, CD28, CD25, CD44 from Becton-Dickinson (Mountain View, Calif., USA). PE-conjugated tetramers (Baylor College of Medicine) and APC-conjugated pentamers (Proimmune Ltd, Oxford, UK), were used to quantify EBV-CTL precursor frequencies. For cell surface and pentamer staining 10,000 and 100,000 live events, respectively, were acquired on a FACSCalibur flow cytometer and the data analyzed using Cell Quest software (Becton Dickinson).

CFSE labeling to measure cell division: To assess the doubling rate of $2\times10^7$ PBMC or EBV-specific CTLs (EBV-CTLs) were washed twice and resuspended in 850 μl 1× phosphate-buffered saline (PBS) containing 0.1% Fetal Bovine Serum (FBS) (Sigma-Aldrich). Prior to staining, an aliquot of carboxy-fluorescein diacetate, succinimidyl ester (CFSE) (10 mM in dimethyl sulfoxide) (Celltrace™ CFSE cell proliferation kit (C34554) Invitrogen) was thawed, diluted 1:1000 with 1×PBS and 150 μl of the dilution was added to the cell suspension (labeling concentration was 1 μM). Cells were incubated with CFSE for 10 minutes at room temperature. Subsequently 1 ml FBS was added to the cell suspension followed by a 10 minute incubation at 37° C. Afterwards cells were washed twice with 1×PBS, counted, and stimulated with antigen as described.

AnnexinV-7-AAD staining: To determine the percentage of apoptotic and necrotic cells in our cultures we performed Annexin-7-AAD staining as per manufacturers' instructions (BD Pharmingen™ #559763, San Diego, Calif.). Briefly, EBV-CTL from the 24-well plates or the G-Rex were washed with cold PBS, resuspended in 1× Binding Buffer at a concentration of $1\times10^6$ cells/ml, stained with Annexin V-PE and 7-AAD for 15 minutes at RT (25° C.) in the dark. Following the incubation the cells were analyzed immediately by flow cytometry.

Chromium release assay: We evaluated the cytotoxic activity of EBV-CTLs in standard 4-hour $^{51}$Cr release assay, as previously described. As desired cells we used autologous and HLA class I and II mismatched EBV-transformed lymphoblastoid cell line (EBV-LCL) to measure MHC restricted and unrestricted killing, as well as the K562 cell line to measure natural killer activity. Chromium-labeled desired cells incubated in medium alone or in 1% Triton X-100 were used to determine spontaneous and maximum $^{51}$Cr release, respectively. The mean percentage of specific lysis of triplicate wells was calculated as follows: [(test counts−spontaneous counts)/(maximum counts−spontaneous counts)]×100.

Enzyme-Linked Immunospot (ELIspot) assay: ELIspot analysis was used to quantify the frequency and function of T cells that secreted IFNγ in response antigen stimulation. CTL lines expanded in 24 well plates or in the G-Rex were stimulated with irradiated LCL (40Gy) or LMP1, LMP2, BZLF1 and EBNA1 pepmixes (diluted to 1 µg/ml) (JPT Technologies GmbH, Berlin, Germany), or EBV peptides HLA-A2 GLCTLVAML=GLC, HLA-A2 CLGGLLTMV=CLG, HLA-A2-FLYALALLL=FLY, and HLA-A29 ILLARLFLY=ILL (Genemed Synthesis, Inc. San Antonio, Tex.), diluted to a final concentration of 2 µM, and CTLs alone served as a negative controls. CTLs were resuspended at $1\times10^6$/ml in ELIspot medium [(RPMI 1640 (Hyclone, Logan, Utah) supplemented with 5% Human Serum (Valley Biomedical, Inc., Winchester, Va.) and 2-mM L-glutamine (GlutaMAX-I, Invitrogen, Carlsbad, Calif.)]. Ninety-six-well filtration plates (MultiScreen, #MAHAS4510, Millipore, Bedford, Mass.) were coated with 10 µg/mL anti-IFN-γ antibody (Catcher-mAB91-DIK, Mabtech, Cincinnati, Ohio) overnight at 4° C., then washed and blocked with ELIspot medium for 1 hour at 37° C. Responder and stimulator cells were incubated on the plates for 20 hours, then the plates were washed and incubated with the secondary biotin conjugated anti-IFN-γ monoclonal antibody (Detector-mAB (7-B6-1-Biotin), Mabtech) followed by incubation with Avidin:biotinylated horseradish peroxidase complex (Vectastain Elite ABC Kit (Standard), #PK6100, Vector Laboratories, Burlingame, Calif.) and then developed with AEC substrate (Sigma, St. Louis, Mo.). Each culture condition was run in triplicate. Plates were sent for evaluation to Zellnet Consulting, New York, N.Y. Spot-forming units (SFC) and input cell numbers were plotted.

Statistical analysis: In vitro data are presented as mean±1 SD. Student's t test was used to determine the statistical significance of differences between samples, and $P<0.05$ was accepted as indicating a significant difference.

Under these culture conditions, the population of antigen-specific T-cells undergoes at least 7 cell doublings after the initial stimulation over the first 7 days, as shown in FIG. 1A. Thus we expect a weekly T-cell expansion of 128-fold (as measured by the frequency of antigen-specific T-cells times the total number of cells in the cell composition). The frequency of tetramer positive cells after the first, second, and third stimulations is shown in FIG. 1B. On day 0 the frequency of T-cells reactive against two EBV tetramers, RAK and QAK was 0.02% and 0.01%, respectively. After a single stimulation on day 0, by day 9 the frequency of tetramer-positive T-cells in the cell composition had increased from 0.02% and 0.01% to 2.7% and 1.25%, respectively. Thus, a 135-fold and 125-fold increase in the percentage of antigen-specific tetramer positive T-cells residing within the cell composition was attained as measured by RAK and QAK. Also, after a single stimulation on stage 1 of culture, day 0, a 1.1 fold increase in the surface density of cells in the cell composition (data not shown) was observed by day 9 (approximately $1.1\times10^6$ cells/cm$^2$ were present). Since the majority of cells within the PBMC composition are not specific for the stimulating antigens, little overall increase in total cell number is observed, but the fold expansion of the antigen-specific cell population within the composition was around 280 during the first stage of culture, as shown in FIG. 1C. Unfortunately, although the number of cell doublings was the same during the second and third stages of culture as measured by CSFE, this rate of antigen-specific T cell expansion was not sustained during the $2^{nd}$ or the $3^{rd}$ stages of culture, being only 5.7 in stage two and 4.3 in stage three. FIG. 2 shows a table that illustrates the discrepancy between the potential expansion and observed fold expansion of antigen-specific T-cells (n=3).

Example 1 demonstrates that the amount of time it takes to produce the desired cells is typically delayed after roughly the first week of production since the rate of population expansion of the desired cells decreases in subsequent stages of culture.

EXAMPLE 2

Reducing the amount of time needed to increase the desired cell population can be achieved by reducing the cell surface density of the desired cell population as the onset of any given stage or stages of culture.

We hypothesized that the decreased rate of expansion of the desired cell population following the second T-cell stimulation compared to the first stimulation was due to limiting cell culture conditions that resulted in activation induced cell death (AICD). For example, referring to FIG. 3A, at the first stimulation, the EBV antigen-specific T-cell component of PBMCs represents, at most, 2% of the population and so the antigen-specific responder T-cell seeding density is less than $2\times10^4$ per cm$^2$, with the remaining PBMC acting as non-proliferating feeder cells (seen as the CFSE positive cells in FIG. 3A) that sustain optimal cell-to-cell contact allowing proliferation of the antigen-specific CTLs. By contrast, at the second stimulation on day 9, the majority of T-cells are antigen-specific, and although the total cell density of the composition is about the same, the proliferating cell density is 50 to 100 fold higher. As a consequence, on re-stimulation the majority of cells proliferate and may therefore rapidly consume and exhaust their nutrients and $O_2$ supply.

To determine whether limiting culture conditions were responsible for sub-optimal T cell growth rates, we measured the expansion of activated T-cells plated at lower cell densities. Methods were as previously described in Example 1.

We seeded activated EBV-specific T-cells in wells of standard 24-well plates, each well having 2 cm$^2$ of growth surface area, at doubling dilutions to create diminishing surface densities ranging from $1\times10^6$/cm$^2$ to $3.1\times10^4$/cm$^2$ while maintaining a responder cell to stimulatory cell ratio (R:S) of 4:1 as shown in FIG. 3B. The maximum CTL expansion (4.7±1.1 fold) was achieved with a starting CTL surface density of $1.25\times10^5$ per $cm^2$, but further dilution decreased the rate of expansion as shown in FIG. 3B. We speculated that this limiting dilution effect was possibly due to lack of cell-to-cell contact, and therefore we cultured doubling dilutions of EBV-CTL from surface densities of $1\times10^6$ to $3.1\times10^4$ with a fixed number of feeder cells (EBV-LCL plated at a surface density of $1.25\times10^5/cm^2$) and assessed cell expansion over a 7 day period. We observed a dramatic increase in CTL expansion from merely 2.9±0.8 fold with EBV-CTL at a surface density of $1\times10^6/cm^2$ all the way to a 34.7±11 fold expansion with EBV-CTL at a surface density of $3.1\times10^4/cm^2$, as presented in FIG. 3C. Importantly, this modification of the culture conditions did not change the function or antigen specificity of the cells (data not shown). A population of activated antigen-specific T cells is therefore capable of greater expansion than conventional culture methods allow. Of note, the maximum surface density achieved after stimulation (1.7 to $2.5\times10^6/cm^2$) was the same regardless of the starting surface density.

Thus, conventional culture conditions were limiting, indicating the medium volume to growth surface area ratio needs to increase beyond the conventional 1 $ml/cm^2$ to allow the desired cell population to move beyond the surface density limits of conventional methods. Additionally, improved expansion of antigen-specific CTL to about 34-fold can be obtained by reducing the surface density of the desired cell population below conventional methods at the onset of any stage of culture. This has substantial ramifications in cell therapy, where the quantity of cells at the onset of production is often quite limited. For example, by distributing the in limited amount of desired cells onto increased surface area at lowered surface density, a greater population of desired cells can be attained in a shorter period of time as the rate of population growth increases dramatically relative to conventional surface density.

EXAMPLE 3

A minimum surface density of a cell population that includes the desired cells and/or antigen presenting cells can allow outgrowth of a desired cell population that is seeded at very low surface density.

Figure 3:
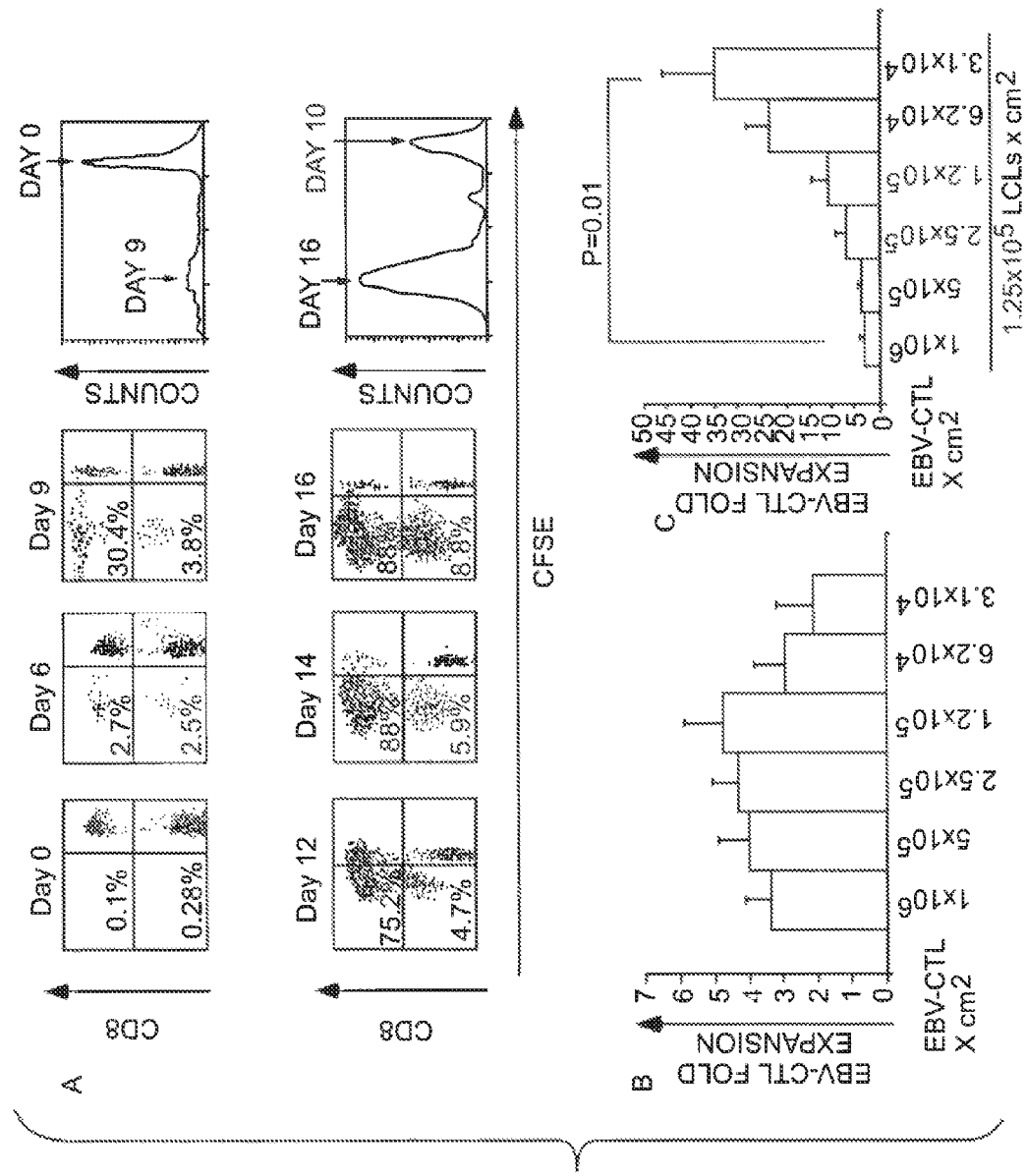
FIG. 3A shows the presence of antigen-specific T-cells following stimulations in Example 2.
FIG. 3B shows the expansion of a population of antigen-specific T-cells as surface densities diminish from $1\times10^6$/cm$^2$ to $3.1\times10^4$/cm$^2$ while maintaining an antigen-specific T-cell to antigen presenting cell ratio of 4:1 in Example 2.
FIG. 3C shows the expansion of a population of antigen-specific T-cells as surface densities diminish from $1\times10^6$/cm$^2$ to $3.1\times10^4$/cm$^2$ while in the presence of a fixed number of antigen presenting cells in Example 2.
Figure 4:
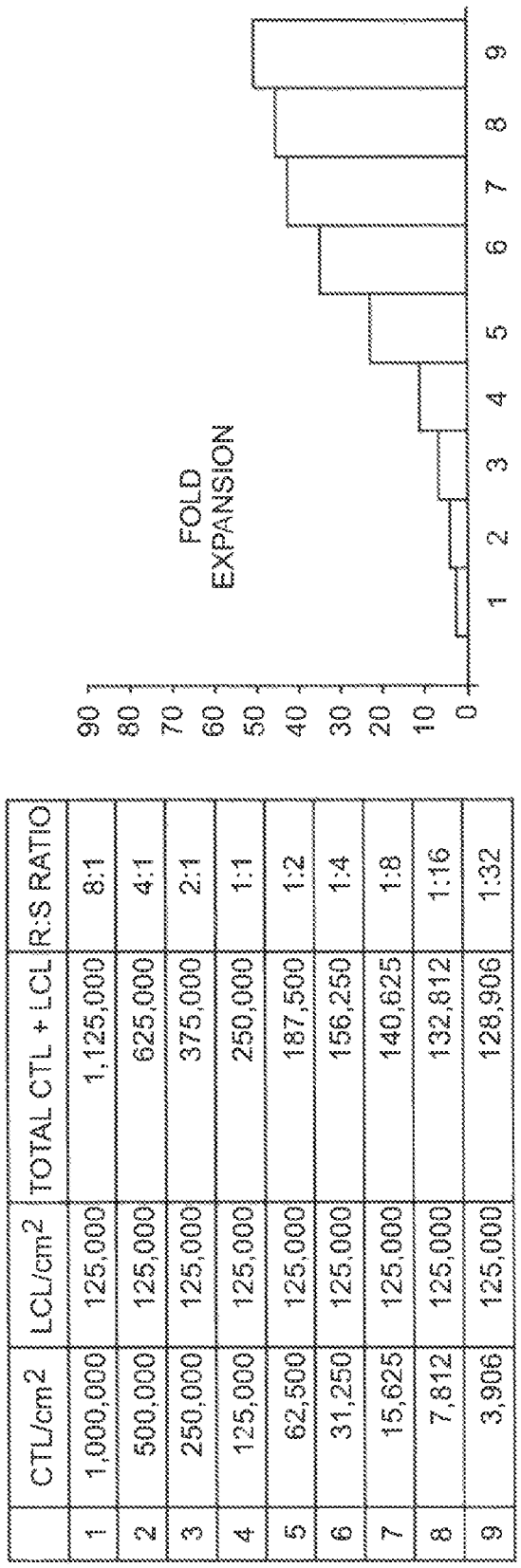
FIG. 4 shows an example of results obtained when continuing the work described in FIG. 3, which further demonstrated that when desired cells need the support of other cells, unconventionally low desired cell surface density can initiate population expansion so long as desired cells are in the presence of an adequate supply of feeder and/or antigen presenting cells.

FIG. 4 shows an example of results we obtained when continuing the work described in FIG. 3, which further demonstrated that when desired cells need the support of other cells, unconventionally low desired cell surface density can initiate population expansion so long as desired cells are in the presence of an adequate supply of feeder and/or antigen presenting cells. In these experiments, we continue to demonstrate how a total cell composition with a surface density and R:S ratio of between about $1.0\times10^6$ desired cells/$cm^2$ at an R:S ratio of 8 to 1 and merely about 3900 desired cells/$cm^2$ at an R:S ratio of 1 to 32 could allow desired cells to be greatly expanded to over 50 fold times the starting surface density, at which point we discontinued testing.

EXAMPLE 4

The ability to allow a production process to repeat in stages by initiating a stage with an unconventionally low desired cell surface density, allowing population expansion, terminating the stage and repeating conditions was demonstrated to deliver repeatable outcomes.

Figure 5:
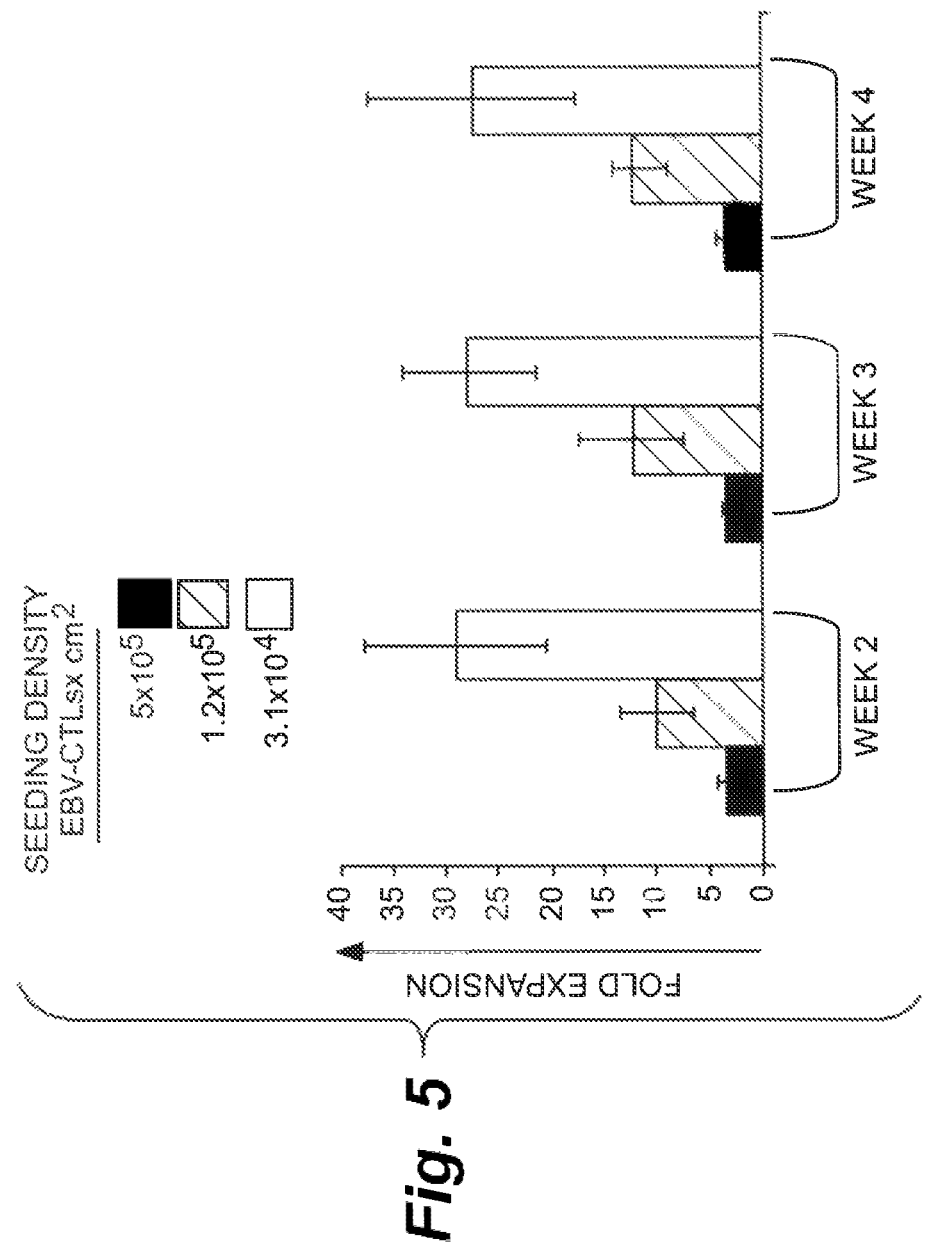
FIG. 5 shows a histogram demonstrating the ability to repeat the magnitude of the population expansion of desired cells by initiating culture at three differing cell surface densities (CTL/cm$^2$).

We continued the assessments described in Example 3 at three of the desired cell surface densities (CTL/$cm^2$) as shown in FIG. 5. Each specific seeding density was able to consistently attain the same fold expansion. The implications will be described in more detail further on as they relate to the ability to dramatically reduce the production time for a desired cell population.

EXAMPLE 5

Culturing desired cells on a growth surface that is comprised of gas permeable material while simultaneously increasing the medium volume to growth surface area ratio increases the number of times a desired cell population can double in a given stage of culture relative to conventional methods and increases the surface density that is attainable.

Cell lines and tumor cells, immunophenotyping, CFSE labeling, AnnexinV-7-AAD staining, chromium release assay, Enzyme-Linked Immunospot (ELIspot) assay, retrovirus production and transduction of T-lymphocytes, and statistical analysis were as described in Example 1.

Figure 6:
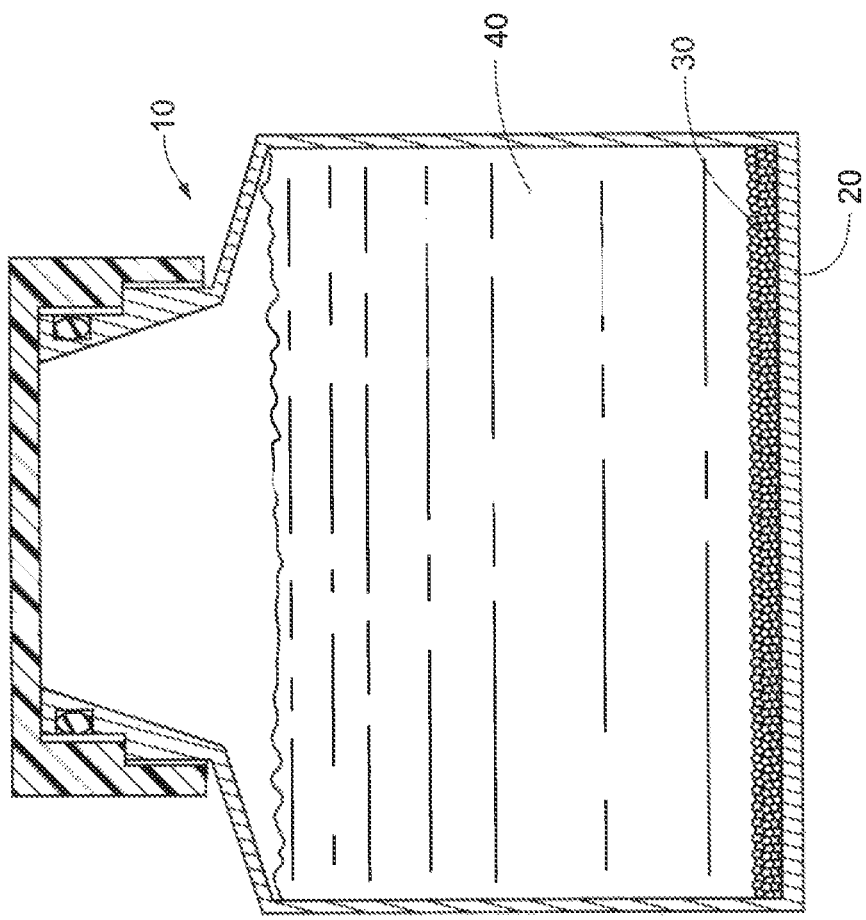
FIG. 6 shows a cross-sectional view of a gas permeable test fixture used to generate data.

Test fixtures (hereinafter generically referred to as "G-Rex") were constructed as shown in FIG. 6. Bottom 20 of each G-Rex 10 was comprised of gas permeable silicone membrane, approximately 0.005 to 0.007 inches thick. Pending U.S. patent application Ser. No. 10/961,814 to Wilson is among many other sources of information relating to the use of alternative gas permeable materials and can be used to educate skilled artisans about gas permeable culture device shapes, features, and other useful characteristics that are beneficial to many of the embodiments of this invention. In this Example 3, G-Rex (referred to as "G-Rex40") had a growth surface area of 10 $cm^2$, upon which a cell composition (shown as item 30) rested, the characteristics of the cell composition varied throughout the experiment as described within. Medium volume (shown as item 40) unless otherwise indicated was 30 mL, creating a medium volume to growth surface area ratio of 3 $ml/cm^2$.

Figure 7:
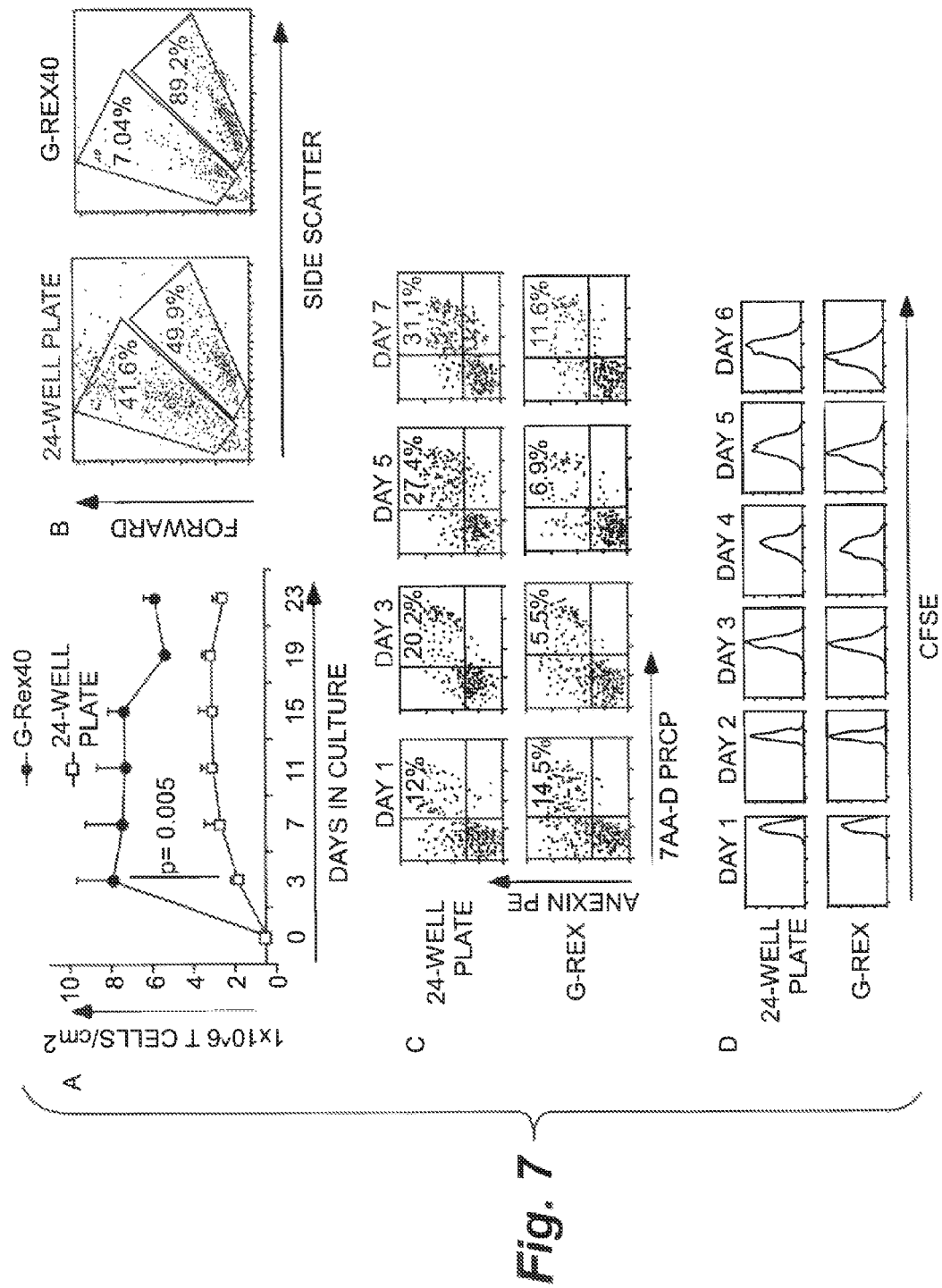
FIG. 7A shows the growth curves of antigen-specific T cells produced in accordance with the present invention in comparison to conventional methods as undertaken in Example 5.
FIG. 7B shows that for Example 5, cell viability was significantly higher in antigen-specific T cells produced in accordance with the present invention in comparison to conventional methods as determined by flow cytometric forward vs. side scatter analysis.
FIG. 7C shows that for Example 5, cell viability was significantly higher in antigen-specific t cells produced in accordance with the present invention in comparison to conventional methods as determined by Annexin-PI 7AAD.
FIG. 7D showed that for Example 5, the superior growth of cells produced in the novel methods of the present invention exhibited the same cell specific growth rate as cell cultured using conventional methods as determined by daily flow cytometric analysis of CFSE labeled cells, confirming that the increased rate of cell expansion resulted from decreased cell death.

Activated EBV-specific CTL and irradiated autologous EBV-LCLs at the conventional 4:1 ratio of CTL:LCL were cultured in G-Rex40 devices. EBV-CTLs were seeded at a surface density of $5\times10^5$ cells/$cm^2$ in the G-Rex40 and the rate of EBV-CTL population expansion was compared with EBV-CTL seeded at the same surface density in a standard 24-well plate with a medium volume to growth surface area of 1 $ml/cm^2$. After 3 days, as shown in FIG. 7A (p=0.005), the EBV-CTLs in the G-Rex40 had increased from $5\times10^5/cm^2$ to a median of $7.9\times10^6/cm^2$ (range 5.7 to $8.1\times10^6/cm^2$) without any medium exchange. In contrast, EBV-CTLs cultured for 3 days in conventional 24-well plates only increased from a surface density of $5\times10^5/cm^2$ to a median of $1.8\times10^6/cm^2$ (range 1.7 to $2.5\times10^6/cm^2$) by day 3. In the G-Rex40, surface density could be further increased by replenishing medium whereas cell surface density could not be increased by replenishing medium or IL2 in the 24-well plate. For example, EBV-CTL surface density further increased in the G-Rex40 to $9.5\times10^6$ cells/$cm^2$ (range $8.5\times10^6$ to $11.0\times10^6/cm^2$) after replenishing the medium and IL-2 on day 7 (data not shown).

To understand the mechanism behind the superior cell expansion in the G-Rex device, we assessed the viability of OKT3-stimulated peripheral blood T cells using flow cytometric forward vs. side scatter analysis on day 5 of culture. EBV-CTLs could not be assessed in this assay due to the presence of residual irradiated EBV-LCL in the cultures, which would interfere with the analysis. As shown in FIG. 7B, cell viability was significantly higher in the G-Rex40 cultures was significantly higher (89.2% viability in the G-Rex40 vs. 49.9% viability in the 24-well plate). We then analyzed the cultures each day for 7 days using Annexin-PI 7AAD to distinguish between live and apoptotic/necrotic cells, and observed consistently lower viability in T-cells expanded in 24 well plates compared to those in the G-Rex, as shown in FIG. 7C. These data indicate the cumulative improved survival of proliferating cells contributed to the increased cell numbers in the G-Rex devices compared to the 24-well plates.

To determine if there was also a contribution from an increased number of cell divisions in the G-Rex versus the 24-well plates, T-cells were labeled with CFSE on day 0 and divided between a G-Rex40 device with a 40 ml medium volume and a 24 well plate with each well at a 2 ml medium volume. Daily flow cytometric analysis demonstrated no differences in the number of cell divisions from day 1 to day 3. From day 3 onwards, however, the population of desired cells cultured in the G-Rex40 continued to increase at a rate that exceeded the diminishing rate of the 2 ml wells, indicating that the culture conditions had become limiting as shown in FIG. 7D. Thus, the large population of desired cells in the G-Rex40 test fixtures resulted from a combination of decreased cell death and sustained proliferation relative to conventional methods.

EXAMPLE 6

By use of unconventionally high ratios of medium volume to growth surface area and use of growth surfaces comprised of gas permeable material, the need to feed culture during production can be reduced while simultaneously obtaining unconventionally high desired cell surface density.

Figure 8:
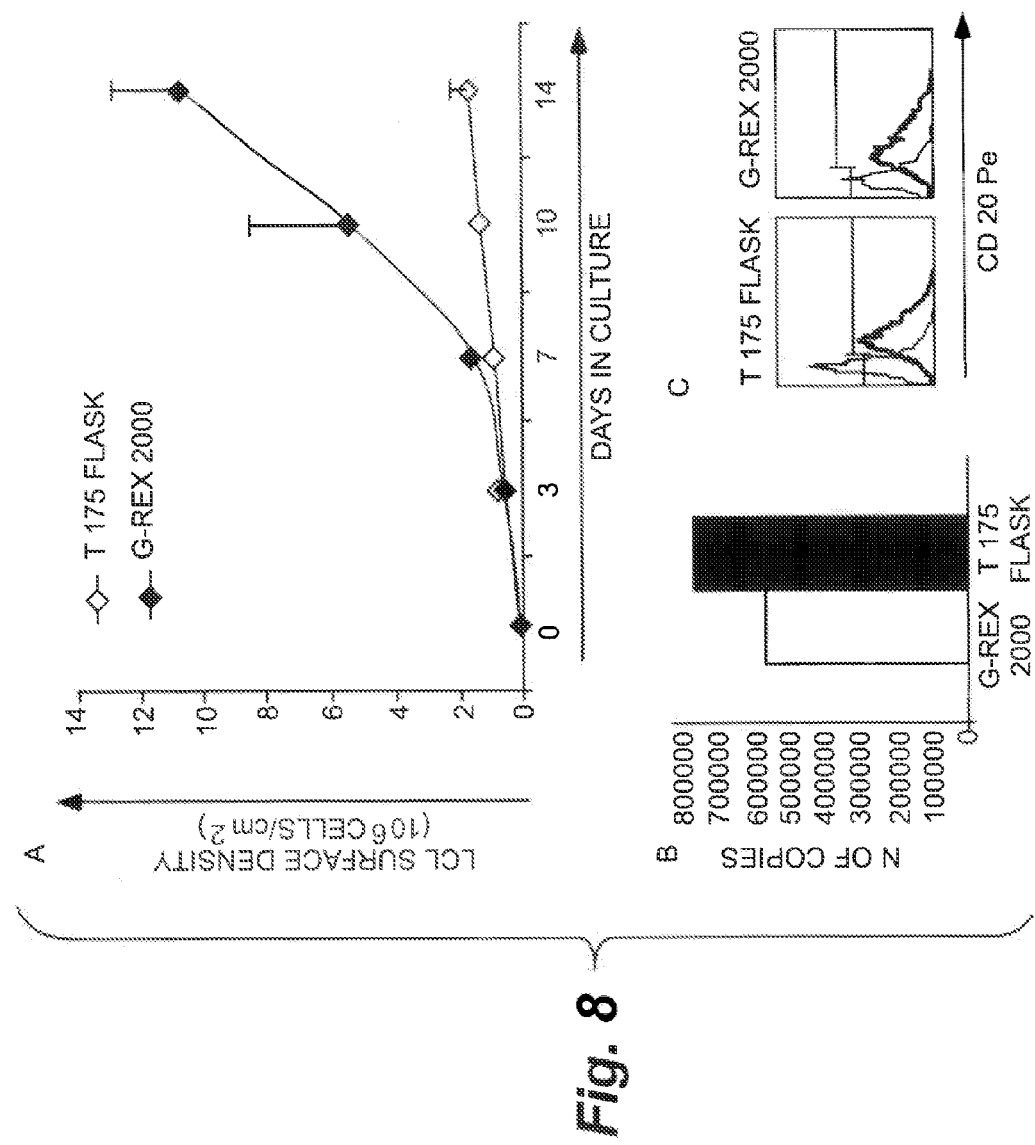
FIG. 8A shows how EVB-CTLs were able to expand beyond what was possible in conventional methods without need to exchange medium.
FIG. 8B shows how the culture condition of Example 6 did not modify the final cell product as evaluated by Q-PCR for EBER.
FIG. 8C shows how the culture condition of Example 6 did not modify the final cell product as evaluated by Q-PCR for B cell marker CD20.

This was demonstrated through use of G-Rex test fixtures for the initiation and expansion of EBV:LCLs. For purposes of this example, G-Rex2000 refers to device as described in FIG. 8, the exception being the bottom is comprised of a 100 $cm^2$ growth surface area and a 2000 ml medium volume capacity is available. EBV-LCLs were cultured in and expand in the G-Rex2000 without changing the cell phenotype. EBV-LCL were plated into a G-Rex2000 at a surface density of $1\times10^5$ cells/$cm^2$ along with 1000 ml of complete RPMI medium to create a medium volume to surface area ratio of 10 ml/$cm^2$. For comparison, EBV-LCL were plated into a T175 flask at a surface density of $5\times10^5$ cells/$cm^2$ along with 30 ml of complete RPMI medium to create a medium volume to surface area ratio of about 0.18 ml/$cm^2$. As presented in FIG. 8A, the EBV-LCL cultured in G-Rex2000 expanded more than those in the T175 flask without requiring any manipulation or media change. This culture condition did not modify the final cell product as evaluated by Q-PCR for EBER and B cell marker CD20 as presented in FIG. 8B and FIG. 8C.

EXAMPLE 7

When sufficient feeder and/or antigen cells are not present at the onset of culture, desired cells may not expand. However, the cell composition can be altered to include an additional cell type acting as feeder cells and/or antigen presenting cell to allow expansion.

Figure 9:
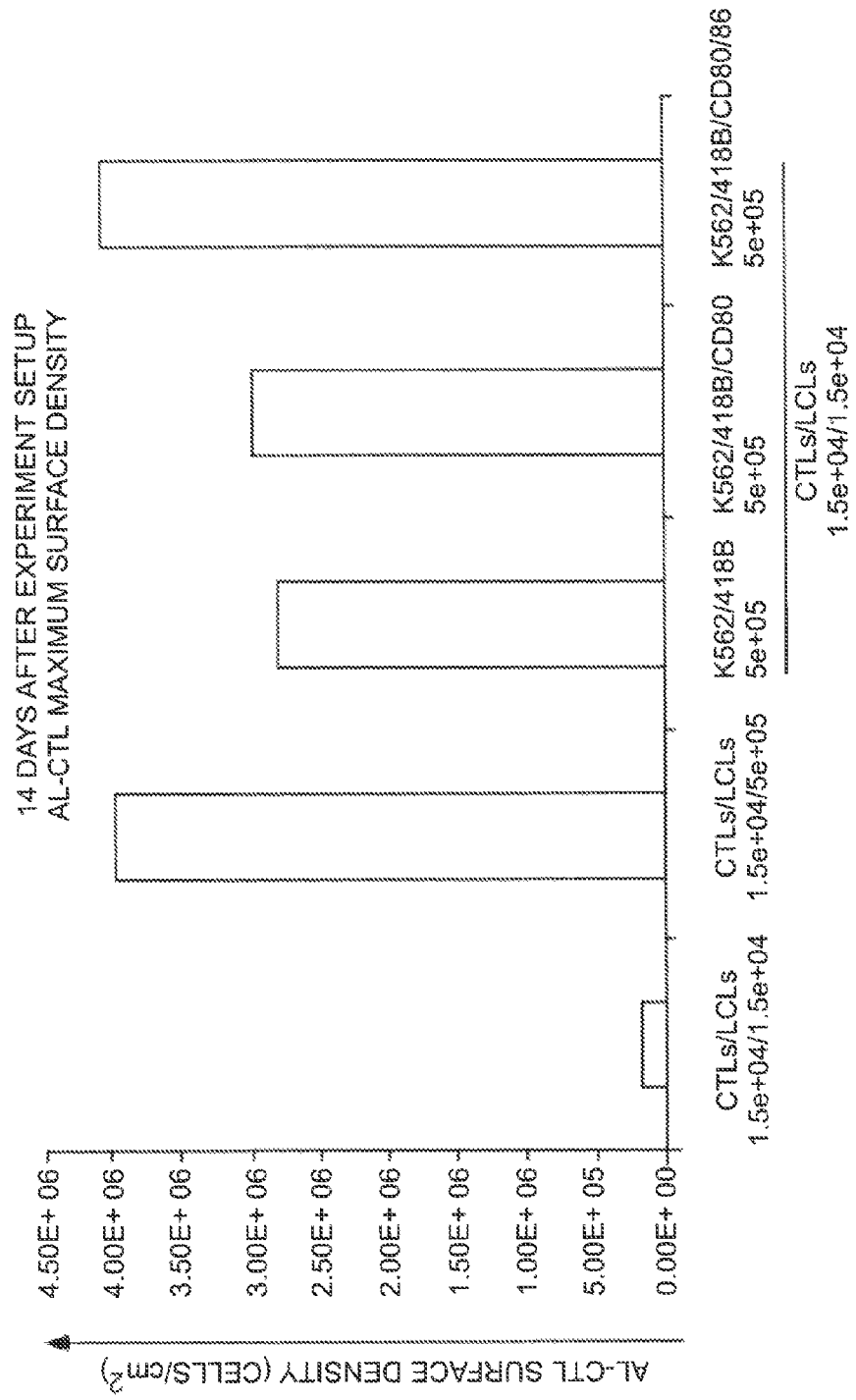
FIG. 9 shows an illustrative example in which we experimentally demonstrated that a very low cumulative surface density of desired cells and antigen presenting cells (in this case AL-CTLs and LCLs cells combining to create a cell composition with a surface density of 30,000 cells/cm$^2$) was unable to initiate outgrowth of the AL-CTL population.

FIG. 9 shows an illustrative example in which we experimentally demonstrated that a very low cumulative surface density of desired cells and antigen presenting cells (in this case AL-CTLs and LCLs cells combining to create a cell composition with a surface density of 30,000 cells/$cm^2$) was unable to initiate outgrowth of the AL-CTL population. However, this same cell composition could be made to grow by altering the composition to include another cell type acting as a feeder cell. In this case we evaluated a feeder layer of three various forms of irradiated K562 cells at a surface density of about $0.5\times10^6$ cells/$cm^2$ and in all cases the population of AL-CTL expanded from the initial cell composition depicted in the first column of the histogram to move from a surface density of just 15,000 cells/$cm^2$ to a surface density of $4.0\times10^6$ cells/$cm^2$ over 14 days. We also demonstrated, as opposed to the addition of a third cell type, increasing the population of LCLs achieved similar favorable results. The high surface density used for the LCL or K562 was arbitrarily chosen to demonstrate that a very low population of desired cells can be used to initiate growth when the cell composition includes an adequate number of feeder and/or antigen specific cells. When feeder cells are in short supply, expensive, or cumbersome to prepare, reducing their surface density to below $0.5\times10^6$ cells/$cm^2$ is recommended. In general, and as we have demonstrated, when antigen presenting cells and/or feeder cells are in the cell composition, the additive surface density of the antigen presenting cells and/or feeder cells and the desired cells should preferably be at least about $0.125\times10^6$ cells/$cm^2$ to create enough surface density in the cell composition to initiate the expansion of the desired cell population. Also, to attain the continued expansion beyond standard surface density limits, the use of growth surfaces comprised of gas permeable material was used in this example along with a medium volume to surface area ratio of 4 ml/$cm^2$.

EXAMPLE 8

Reduced desired cell surface densities, altered responder cell to stimulatory cell ratios, increased medium to growth surface area ratios, and periodic distribution of cells at a low surface density culture onto growth surfaces comprised of gas permeable material allow more desired cells to be produced in a shorter period of time and simplifies the production process when compared to other methods.

To further evaluate our ability to simplify and shorten the production of desired cells, we used G-Rex test fixtures for the initiation and expansion of EBV-CTLs. For purposes of this example, G-Rex500 refers to device as described in FIG. 6, the exception being the bottom is comprised of a 100 $cm^2$ growth surface area and a 500 ml medium volume capacity is available.

For the initial stage of EBV-CTL production, we seeded PBMCs in the G-Rex40 at a surface density of $1\times10^6$/$cm^2$ (total=$10^7$ PBMCs distributed over 10 $cm^2$ growth surface area of the G-Rex40) and stimulated them with EBV-LCL using a 40:1 ratio of PBMC:EBV-LCL. For CTL production, this 40:1 ratio is preferable in the first stimulation to maintain the antigen-specificity of the responder T-cells. After the initial stage of culture, a second stage was initiated on day 9, wherein $1\times10^7$ responder T-cells were transferred from the G-Rex40 to a G-Rex500 test fixture. To initiate stage two of culture, 200 ml of CTL medium was placed in the G-Rex500, creating a medium volume to surface area ratio at the onset of stage two of 2 ml/$cm^2$ medium height at 2.0 cm above the growth surface area. The surface density of desired cells at the onset of stage two was $1\times10^5$ CTL/$cm^2$ with antigen presenting cells at a surface density of $5\times10^5$ LCL/$cm^2$, thereby creating a non-conventional 1:5 ratio of desired cells to antigen presenting cells. This stage two cell surface density and R:S ratio produced consistent EBV-CTL expansion in all donors screened. Four days later (day 13), IL-2 (50 U/ml—final concentration) was added directly to the culture, as was 200 ml of fresh medium, bringing medium volume to surface area ratio to 4 ml/$cm^2$. On day 16, the cells were harvested and counted. The median surface density of CTLs obtained was $6.5\times10^6$ per $cm^2$ (range $2.4\times10^6$ to $3.5\times10^7$).

Figure 10:
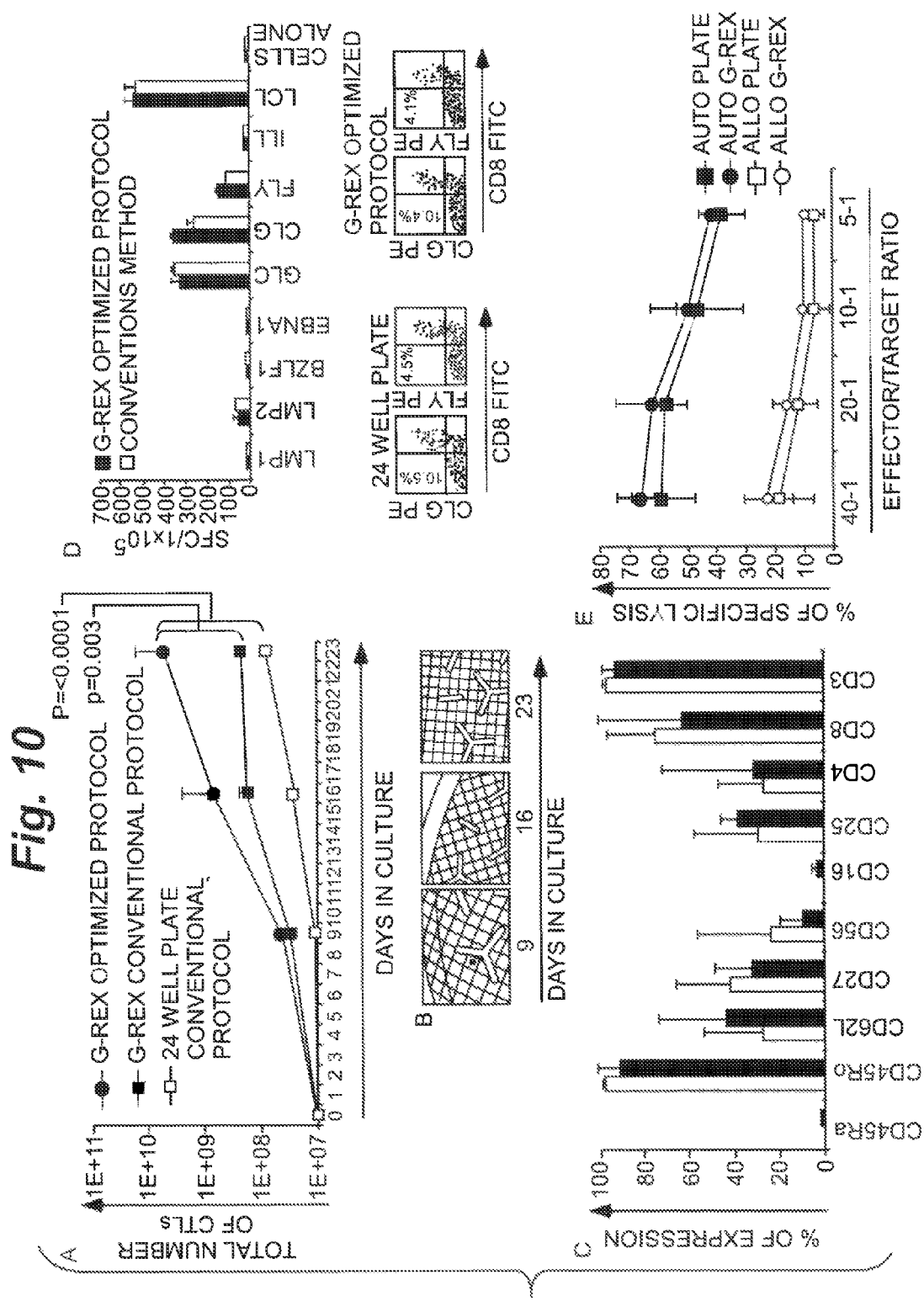
FIG. 10A presents data of Example 8 that show how two novel methods of culturing cells produce more cells over a 23 day period than a conventional method.
FIG. 10B shows a photograph of cells cultured in a test fixture in Example 8.
FIG. 10C shows that in Example 8, the two novel methods of culture and the conventional method all produce cells with the same phenotype.
FIG. 10D shows that for Example 8, a representative culture in which T-cells stimulated with EBV peptide epitopes from LMP1, LMP2, BZLF1 and EBNA1 of EBV and stained with HLA-A2-LMP2 peptide pentamers staining showed similar frequencies of peptide-specific T-cells.
FIG. 10E shows that for the novel methods and the conventional method of Example 8, cells maintained their cytolytic activity and specificity and killed autologous EBV-LCL, with low killing of the HLA mismatched EBV-LCL as evaluated by $^{51}$Cr release assays.

Compared to conventional protocols, the use of growth surfaces comprised of gas permeable material allows increased medium volume to surface area ratios (i.e. greater than 1 ml/cm$^2$), lower cell surface densities (i.e. less than 0.5×10$^6$/cm$^2$), and altered ratios of responder to stimulator cells (less than 4:1) to create a decrease in production time. FIG. 10A shows the comparison of this G-Rex approach of Example 8 to the use of conventional methods of Example 1 and the G-Rex approach described in Example 5. As shown, the conventional method needed 23 days to deliver as many desired cells as could be delivered in either G-Rex method in about 10 days. After 23 days, the G-Rex approach of Example 8 was able to produce 23.7 more desired cells than the G-Rex method of Example 5 and 68.4 times more desired cells than the conventional method of Example 1. Furthermore, the desired cells continued to divide until day 27-30 without requiring additional antigen presenting cell stimulation provided the cultures were split when cell surface density was greater than 7×10$^6$/cm$^2$.

Although the CTLs could not be viewed clearly in the G-Rex using light microscopy, clusters of CTLs could be visualized by eye or by inverted microscope and the appearance of the cells on days 9, 16, and 23 of culture is shown in FIG. 10B. Culture in the G-Rex did not change the phenotype of the expanded cells as shown in FIG. 10C, with greater than 90% of the cell composition being CD3+ cells (96.7±1.7 vs. 92.8±5.6; G-Rex vs. 24-well), which were predominantly CD8+ (62.2%±38.3 vs. 75%±21.7). Evaluation of the activation markers CD25 and CD27, and the memory markers CD45RO, CD45RA, and CD62L, demonstrated no substantive differences between EBV-CTLs expanded under each culture condition. The antigen specificity was also unaffected by the culture conditions, as measured by ELIspot and pentamer analysis. FIG. 10D shows a representative culture in which T-cells stimulated with EBV peptide epitopes from LMP1, LMP2, BZLF1 and EBNA1 and stained with HLA-A2-LMP2 peptide pentamers staining showed similar frequencies of peptide-specific T-cells. Further, the expanded cells maintained their cytolytic activity and specificity and killed autologous EBV-LCL (62%±12 vs. 57%±8 at a 20:1 E:T ratio; G-Rex vs. 24-well plate), with low killing of the HLA mismatched EBV-LCL (15%±5 vs. 12%±7 20:1 ratio) as evaluated by $^{51}$Cr release assays as shown in FIG. 10E.

Discussion of various novel methods for improved cell production for cell therapy: Examples 1-8 have been presented to demonstrate to skilled artisans how the use of various conditions including reduced surface density of the desired cell population at the onset of a production cycle, reduced surface density ratios between responder cells and stimulating cells, growth surfaces comprised of gas permeable materials, and/or increased medium volume to growth surface area ratios can be used to expedite and simplify the production of cells for research and clinical application of cell therapy. Although Examples 1-8 were related to the production of antigen specific T cells, these novel culture conditions can be applied to many important suspension cell types with clinical relevance (or required for pre-clinical proof of concept murine models) including regulatory T cells (Treg), natural killer cells (NK), tumor infiltrating lymphocytes (TIL), primary T lymphocytes, a wide variety of antigen specific cells, and many others (all of which can also be genetically modified to improve their function, in-vivo persistence or safety). Cells can be expanded with feeder cells and/or antigen presenting cells that can include PBMC, PHA blast, OKT3 T, B blast, LCLs and K562, (natural or genetically modified to express and antigen and/or epitope as well as co-stimulatory molecules such as 41BBL, OX40L, CD80, CD86, HLA, and many others) which may or may not be pulsed with peptide and/or a relevant antigen.

Unconventionally Low Initial Surface Density: One aspect of the present invention is the discovery that production time can be reduced relative to conventional methods by the use of lower desired cell surface density. In this manner, desired cells are able to have a greater numerical difference between their minimum and maximum cell surface densities than conventional methods allow. Preferably, when the rate of desired cell population growth has begun to diminish, but the quantity of desired cells is not yet sufficient to terminate production, the desired cells are re-distributed upon additional growth surfaces comprised of gas permeable material at low starting surface density once again.

Figure 11:
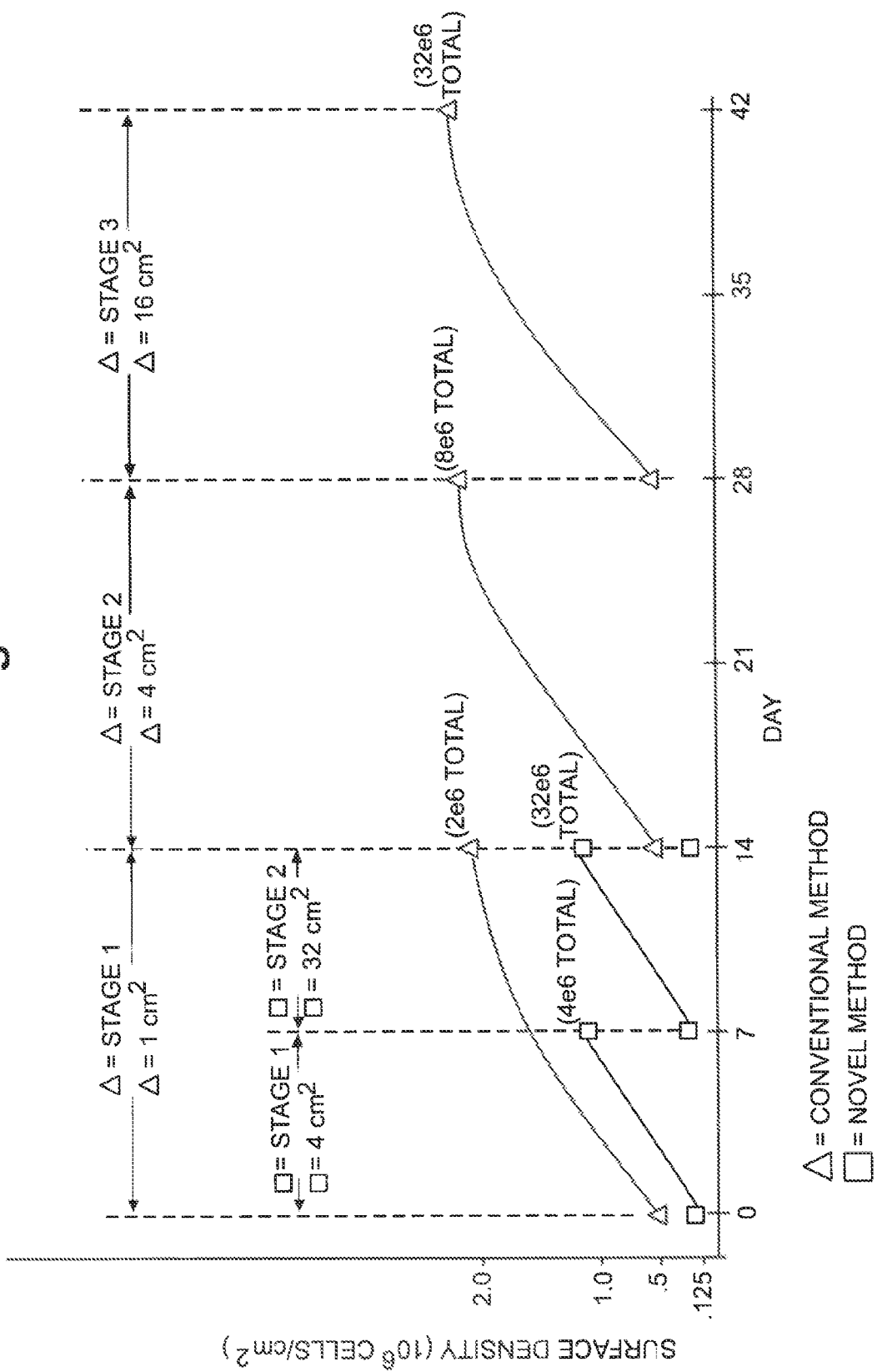
FIG. 11 shows a graphical representation of expansion of a desired cell population on a growth surface under the conventional scenario as compared to population expansion of the desired cell type using one aspect of the present invention.

To explain how our novel cell production methods that rely upon lower surface density at the onset of any given culture stage can be applied, an example is now described. FIG. 11 shows a graphical representation of expansion of a desired cell population on a growth surface under the conventional scenario as compared to population expansion of the desired cell type using one aspect of the present invention. In this novel method, the surface density of desired cells at the onset of a production stage is less than conventional surface density. In order to make the advantages of this novel method the focus, this explanation does not describe the process of initially obtaining the desired cell population. The "Day" of culture starts at "0" to allow skilled artisans to more easily determine the relative time advantages of this novel method. In this example, each production cycle of the conventional method begins at a conventional surface density of 0.5×10$^6$ desired cells/cm$^2$ while each production cycle of this example begins at a much lower and unconventional surface density of 0.125×10$^6$ desired cells/cm$^2$. Thus, 4 times more surface area (i.e. 500,000/125,000) is required in this example to initiate the culture of than the conventional methods require. In this example, the desired cells of the conventional method reaches a maximum surface density of 2×10$^6$ cells/cm$^2$ in 14 days. Thus, 1 cm$^2$ of growth area delivers 2×10$^6$ cells/cm$^2$ which are then re-distributed onto 4 cm$^2$ of growth area so that production can be continued using the conventional starting density of 0.5×10$^6$ cells/cm$^2$ (i.e. 4 cm$^2$ times 0.5×10$^6$ cells=2×10$^6$ cells). The cycle repeats for another 14 days at which point maximum cell surface density is again reached, with each of the 4 cm$^2$ of growth surface area delivering 2.0×10$^6$ cells for a total of 8.0×10$^6$ cells that are then distributed onto 16 cm$^2$ of growth area and the growth cycle repeats to deliver a total of 32×10$^6$ cells over 42 days.

The novel method depicted in FIG. 11, instead of using the conventional method of depositing 500,000 desired cells onto 1 cm$^2$ at the onset of production, distributes the 500,000 cells equally onto 4 cm$^2$ of growth area to create at unconventionally low starting surface density of 125,000 desired cells/cm$^2$ on Day 0. In example the novel method, as with the conventional method, has its growth rate about to diminish on Day 7. Cells in the novel method are at a surface density of 1×10$^6$ cells/cm$^2$. Thus, at the time point where growth rate is about to diminish, this stage of culture has produced 4×10$^6$ cells that are then re-distributed onto 32 cm$^2$ of growth area so that production in Stage 2 can be continued using the starting surface density of 0.125×10$^6$ cells/cm$^2$ (i.e. 32 cm$^2$ times 0.125×10$^6$ cells=4×10$^6$ cells). The cycle, or stage, of production repeats for another 7 days to Day 14, at which point maximum cell surface density is again reached, with each of the 32 cm$^2$ of growth surface area containing 1.0×10$^6$ desired cells to yield a total of 32×10$^6$ cells in just 14 days. Note how at the end of each production cycle, as with the conventional method, the novel method delivers a multiple of the finishing surface density divided by the starting surface density. However, by lowering starting cell surface density and completing each stage of production before cells have entered a growth production time is dramatically lowered. This example that describes how, by lowering the desired cell surface density (in this case to $0.125 \times 10^6$ cells/cm$^2$) relative to conventional cell surface density, the same quantity of desired cells are delivered in just 33% of the time as the conventional method (14 days vs. 42 days).

Although we quantified the advantages using a starting surface density of $0.125 \times 10^6$ cells/cm$^2$, skilled artisans should be aware that this example of the present invention demonstrates that any reduction below conventional cell surface density will reduce production duration. Furthermore, skilled artisans will recognize that in this and other novel methods presented herein, the rate of cell growth and point at which diminished cell growth occurs described is for illustrative purposes only and the actual rates will vary in each application based on a wide variety of conditions such as medium composition, cell type, and the like. Additionally, for a given application, skilled artisans will recognize that the advantage of this aspect of the present invention is the production time reduction resulting from the reduction of cell surface density below that of conventional cell surface density in any particular application, wherein the particular conventional surface density used in this illustrative example may vary from application to application.

Thus, one aspect of the methods of the present invention when there is a desire to minimize the duration of production for a given quantity of desired cells that reside within a cell composition by use of reduced cell surface density is now described. Desired cells should be deposited upon a growth surface at an unconventionally low cell surface density such that:

a. the desired cells are in the presence of antigen presenting cells and/or feeder cells and with medium volume to surface area ratio of up to 1 ml/cm$^2$ if the growth surface is not comprised of gas permeable and up to 2 ml/cm$^2$ if the growth surface is comprised of gas permeable, and b. the preferred surface density conditions at the onset of a production cycle being such that the target cell surface density is preferably less than $0.5 \times 10^6$ cells/cm$^2$ and more preferably diminishing as described in FIG. 4, and c. the surface density of the desired cells plus the surface density of the antigen presenting cells and/or feeder cells is preferably at least about $1.25 \times 10^5$ cells/cm$^2$.

Based on the examples above, it is advisable for one to verify that the expansion of the desired cell population does not become limited if there is an attempt to further reduce the surface density of the antigen presenting cells and/or feeder cells below $1.25 \times 10^5$ cells/cm$^2$. We selected $1.25 \times 10^5$ cells/cm$^2$ based on the goal of demonstrating that outgrowth of a population of desired cells at unconventionally low density can be achieved when augmented by an adequate supply of antigen presenting cells and/or feeder cells.

Use of growth surfaces comprised of gas permeable material and higher medium volume to growth surface area ratios can simplify and shorten production. Another aspect of the present invention is the discovery that the use of growth surfaces comprised of gas permeable material and medium volume to growth surface area ratios that exceed conventional ratios, and repeated cycles of production that increase the amount of growth surface area used over time will reduce production duration.

Figure 12:
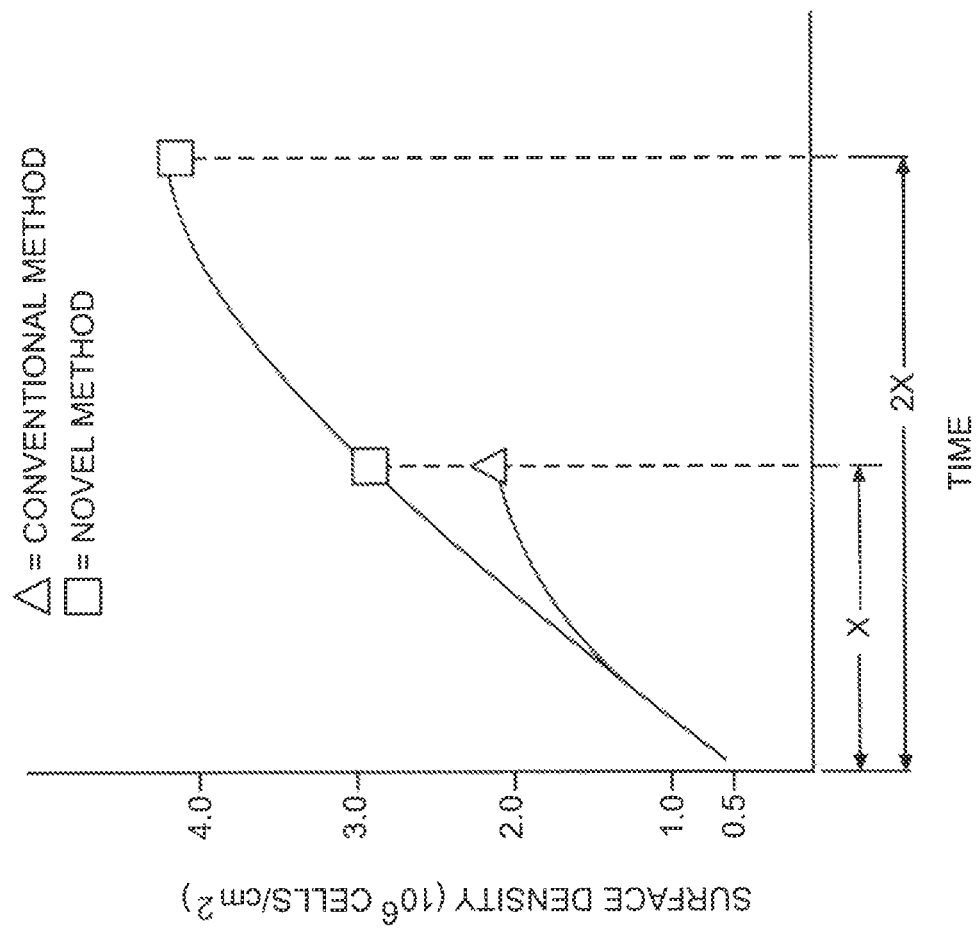
FIG. 12 shows an example of the advantages that can be obtained by utilizing a growth surface comprised of gas permeable material and an unconventionally high medium volume to growth surface area ratio beyond 1 or 2 ml/cm$^2$.

An illustrative example is now presented to show how these conditions can reduce the duration of production. FIG. 12 augments the discussion to show an example of the advantages that can be obtained by utilizing a growth surface comprised of gas permeable material and an unconventionally high medium volume to growth surface area ratio beyond 1 or 2 ml/cm$^2$. The discussion that follows is intended to demonstrate to skilled artisans how, by use of such a method, several options become available including reducing production time, reducing the amount of growth surface area used, and/or reducing labor and contamination risk. Skilled artisans will recognize that FIG. 12 and associated discussion is merely an example, and does not limit the scope of this invention.

The cell composition containing the desired cell population in this illustrative example is assumed to consume about 1 ml per "X" period of time. FIG. 12 shows two production processes, labeled "conventional method" and "novel method." At the onset of growth, each process begins with desired cells at a surface density of $0.5 \times 10^6$/cm$^2$. However, the growth surface of in the novel method is comprised of gas permeable material and medium volume to surface area ratio is 2 ml/cm$^2$ as opposed to the conventional method of 1 ml/cm$^2$. In time period "X", the desired cell population of the conventional method has a reached a surface density plateau of $2 \times 10^6$/cm$^2$ and is depleted of nutrients while the additional medium volume of the novel method has allowed growth to continue and desired cell surface density is $3 \times 10^6$/cm$^2$. If the novel method continues, it reaches a surface density of $4 \times 10^6$/cm$^2$. Thus, many beneficial options accrue. The novel method can be terminated prior to time "X" with more cells produced than the conventional method, can be terminated at time "X" with about 1.5 times more cells produced than the conventional method, or can continue until the medium is depleted of nutrients with 2 times many desired cells produced as the conventional method in twice the time but without any need to handle the device for feeding. In order for the conventional method to gather as many cells, the cells must be harvested and the process reinitiated, adding labor and possible contamination risk. Since cell therapy applications typically only are able to start with a fixed number of cells, the conventional method does not allow the option of simply increasing surface area at the onset of production.

Figure 13:
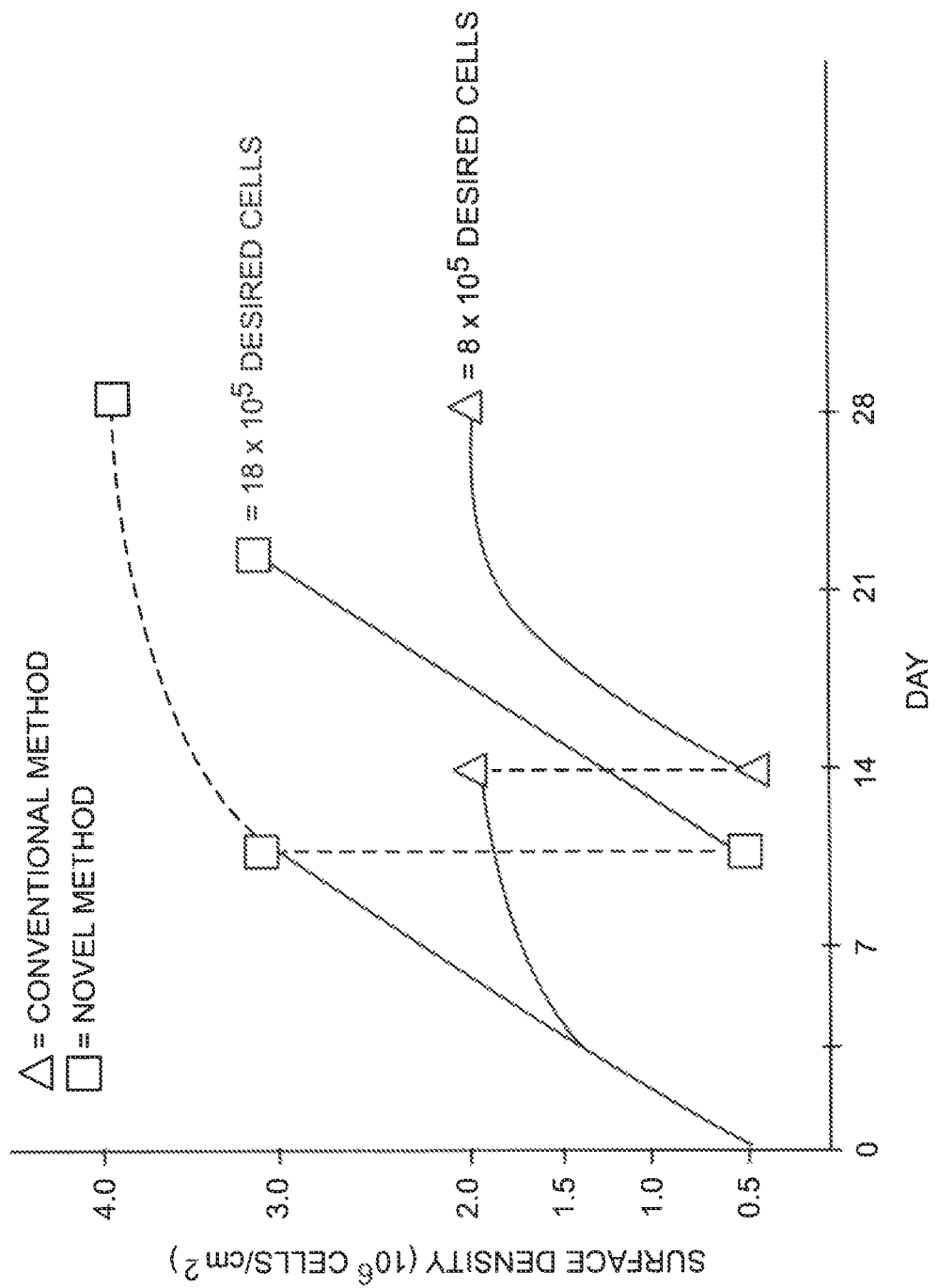
FIG. 13 shows a graphical representation of a novel method of expansion of a desired cell population on a growth surface under the conventional scenario as compared to population expansion of the desired cell type under one embodiment of the present invention in which the cell surface density at the completion of is much greater than conventional surface density.

FIG. 13 continues the example of FIG. 12 to show how more than one production cycle can be of further benefit. FIG. 13 shows a graphical representation of expansion of a desired cell population on a growth surface under the conventional method as compared to population expansion of the desired cell type under one novel method of the present invention in which the surface density of the novel method exceeds surface density of the conventional method. In order to make this embodiment the focus, this explanation does not describe the process of obtaining the desired cell population. The "Day" of culture starts at "0" to allow skilled artisans to more easily determine the relative time advantages of this aspect of the invention. In this example, both cultures are initiated using conventional desired cell surface density of $0.5 \times 10^5$ cells/cm$^2$ at "Day 0". In this illustrative example, the growth surface of the conventional method is also comprised of gas permeable material. However, the medium volume to growth surface ratio in the conventional method is 1 ml/cm$^2$ as opposed to 4 ml/cm$^2$ in the novel method. As shown in FIG. 13, the desired cell population in the conventional method begins to diminish in growth rate when it is at a surface density of about $1.5 \times 10^6$ cells/cm$^2$ in about 4 days and reaches a maximum surface density of $2 \times 10^6$ cells/cm$^2$ in 14 days. At that point the desired cell population is distributed to 4 cm$^2$ of growth area at a surface density of $0.5 \times 10^6$/cm$^2$ in fresh medium at 1.0 ml/cm$^2$ and the production cycle begins again, reaching a surface density of $2 \times 10^6$ cells/cm$^2$ in another 14 days and delivering $8 \times 10^6$ desired cells in 28 days. By comparison, the desired cell population in the novel method begins to diminish in growth rate when it is at a surface density of about $3 \times 10^6$ cells/cm² in roughly about 10 to 11 days and could reach a maximum surface density of 4×10⁶ cells/cm² in 28 days. However, to accelerate production, the cycle ends when the desired cell population is still in a high rate of growth. Thus, at about 10 to 11 days the 3×10⁶ cells are re-distributed to 6 cm² of growth surface area at a surface density of 0.5×10⁶/cm² in fresh medium at 4.0 ml/cm² and the production cycle begins again, with the desired cell population reaching a surface density of 3×10⁶ cells/cm² in roughly another 10 to 11 days and delivering 18×10⁶ desired cells around 21 days. Thus, in about 75% of the time, the novel method has produced over 2 times the number of desired cells as compared to the conventional method.

We have been able to obtain cell surface density in excess of 10×10⁶ cells/cm² upon growth surfaces comprised of gas permeable material, demonstrating that the use of the high surface density aspect of our invention is not limited to the density described in this example.

Thus, another example of the methods of the present invention when there is a desire to minimize the duration of production for a given quantity of desired cells that reside within a cell composition by use of reduced cell surface density is now described:

a. seeding the desired cells upon a growth surface area comprised of gas permeable material and in the presence of antigen presenting cells and/or feeder cells and with medium volume to surface area ratio of at least 2 ml/cm², and b. establishing the preferred surface density conditions at the onset of a production cycle such that the target cell surface density is within the conventional density of about 0.5×10⁶ cells/cm², and c. allowing the desired cell population to expand beyond the conventional surface density of about 2×10⁶ cells/cm², and d. if more of the desired cells are wanted, redistributing the desired cells to additional growth surface comprised of gas permeable material and repeating steps a-d until enough desired cells are obtained.

When using these novel methods, further benefits can be attained by combining the attributes of initiating culture using unconventionally low surface area, using novel surface density ratios of desired cells and/or feeder cells, utilizing a growth surface area comprised of gas permeable material, utilizing unconventionally high ratios of medium volume to growth surface area, and conducting production in cycles. The conditions can be varied at any cycle of production to achieve the desired outcomes, such as striking a balance between reduced production time, surface area utilization, feeding frequency, and the like.

Figure 14:
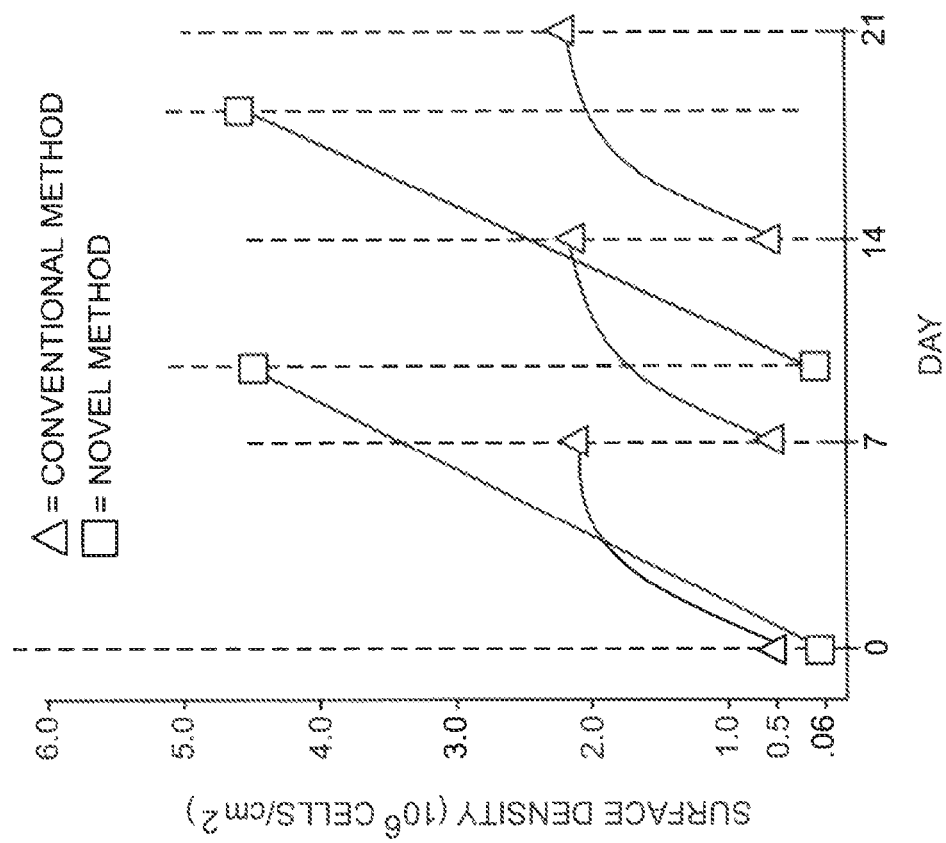
FIG. 14 shows another novel method of cell production that provides yet further advantages over conventional methods.

FIG. 14 shows another novel method in which still further advantages relative to conventional methods are obtained. As with other illustrative embodiments described herein, skilled artisans will recognize that the description herein does not limit the scope of this invention, but instead acts to describe how to attain advantages of improved production efficiency.

In this example, desired cells are doubling weekly in conventional conditions. The "Day" of culture starts at "0" to allow skilled artisans to more easily determine the relative time advantages of this embodiment. Also, issues previously described related to feeder and/or antigen presenting cell surface density ratios are not repeated to simplify this example. For illustrative purposes, assume a starting population of 500,000 desired cells with a doubling time of 7 days in conventional conditions is present on "day 0" production. The conventional method begins with a surface density of 0.5×10⁶ cells/cm² and a medium volume to surface area ratio of 1 ml/cm². As shown, when the population of the desired cells reaches a surface density of 2×10⁶ cells/cm² the cells are distributed onto additional surface area at a surface density of 0.5×10⁶ cells/cm² and the production cycle begins anew. The novel method of this example begins with a surface density of 0.06×10⁶ cells/cm², a growth surface area comprised of gas permeable material, and a medium volume to surface area ratio of 6 ml/cm². As shown, when the population is nearing the start of a growth plateau, cells are redistributed to more growth surface area. In this case, the population is determined to be reaching plateau from noting that plateau is initiated in the conventional method when cell surface density approaches 1.5 times the medium volume to surface area ratio (i.e. about 1.5×10⁶ cells/ml). Thus, at a surface density of about 4.5×10⁶ cells/cm² at about 9 days, cells are distributed onto 36 cm² of growth surface area and the production cycle begins anew.

FIG. 15 tabulates a comparison of each production method depicted in FIG. 14, and extends to stages to demonstrate the power of the novel method, and why it is wise to adjust the production protocol at various stages to fully capture the efficiency. Note that the novel method overpowers the conventional method after completing just the second stage of the production cycle, delivering nearly 1.37 times more cells in only about half the time with just 61% of the surface area requirement. However, note how the third stage of the production cycle creates a massive increase in cells and a corresponding increase in surface area. Thus, one should model the production cycles to anticipate how to adjust the initial cell surface density and/or final cell surface density throughout each cycle of the process to attain an optimal level of efficiency for any given process.

As an example, FIG. 16 shows an example of how one could alter variables in the novel method to gain efficiency as production progresses. For example, an increase in the starting surface density of cycle 3 from 0.06 to 0.70 cell/cm² and a change to the final surface density from 4.5 to 7.5 cells/cm² can be undertaken. Increasing the final surface density is a matter of increasing the medium volume to surface area ratio beyond the initial 6 ml/cm² to a greater number. The greater the medium volume to surface area, the longer the cycle remains in rapid growth phase (i.e. the population expansion prior to plateau). In this case we have allowed 5 extra days to complete the rapid growth phase and raised the medium volume to surface area ratio to about 8 ml/cm². So doing, in this example, allows over 3 trillion cells to be produced in 34 days with a reasonable surface area. For example, we have fabricated and tested devices with about 625 cm² of growth surface comprised of gas permeable material. This is clearly a superior approach to producing cells than the conventional method.

Thus, another preferred embodiment of the methods of the present invention when there is a desire to minimize the duration of production for a given quantity of desired cells that reside within a cell composition by use of reduced cell surface density is now described:

a. seeding the desired cells upon a growth surface area comprised of gas permeable material and in the presence of antigen presenting cells and/or feeder cells and with medium volume to surface area ratio of at least 2 ml/cm², and b. establishing the preferred surface density conditions at the onset of a production cycle such that the target cell surface density is less than the conventional density, preferably at between about 0.5×10⁶ desired cells/cm² and about 3900 desired cells/cm² and total number of desired cells and antigen presenting cells and/or feeder cells being at least about $1.25 \times 10^5$ cells/cm$^2$, and c. allowing the desired cell population to expand beyond the conventional surface density of about $2 \times 10^6$ cells/cm$^2$, and d. if more of the desired cells are wanted, redistributing the desired cells to additional growth surface comprised of gas permeable material and repeating steps a-d until enough desired cells are obtained.

Each of the applications, patents, and papers cited in this application and as well as in each document or reference cited in each of the applications, patents, and papers (including during the prosecution of each issued patent; "application cited documents"), pending U.S. patent application Ser. No. 10/961,814, and each of the PCT and foreign applications or patents corresponding to and/or claiming priority from any of these applications and patents, and each of the documents cited or referenced in each of the application cited documents, are hereby expressly incorporated herein.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims for the present invention, it is expressly intended that the provisions of Section 112, sixth paragraph of 35 U.S.C. are not to be invoked unless the specific terms "means for" or "step for" are recited in a claim.

Those skilled in the art will recognize that numerous modifications can be made to this disclosure without departing from the spirit of the inventions described herein. Therefore, it is not intended to limit the breadth of the invention to embodiments and examples described. Rather, the scope of the invention is to be interpreted by the appended claims and their equivalents.

What is claimed is:

1. An improved method of producing cells comprising:
    growing activated antigen-specific T cells in the presence of irradiated antigen-presenting cells-on a growth surface and with a medium volume to surface area ratio of up to 1 ml/cm$^2$;
    wherein said surface density of the antigen-specific T cells plus the surface density of said antigen presenting cells is between 128,906 and 1,125,000 cells/cm$^2$ and the surface density of the antigen-specific T cells is less than 250,000 cells/cm$^2$ and the combined number of said antigen presenting cells and antigen-specific T cells is less than 500,000 cells/cm$^2$ at the onset of a production cycle.

2. The method of claim 1 wherein growing antigen-specific T cells includes more than one production cycle.

3. The method of claim 1 wherein said antigen-specific T cells are Epstein Barr Virus Cytotoxic T lymphocytes.

4. The method of claim 1 wherein the method is a static cell culture method.

5. The method of claim 1 wherein the growth surface resides in a standard 24 well plate.

6. A method of producing cells comprising:
    Growing activated antigen specific T cells on a growth surface wherein said antigen specific T cells reside at a surface density of between $3.1 \times 10^4$ and $6.2 \times 10^4$ antigen specific T cells per cm$^2$ of growth surface area and in the presence of antigen presenting cells residing at ratio of between 2 and 32 times the number of antigen specific T cells.

7. The method of claim 6 including more than one production cycle.

8. The method of claim 6 wherein said antigen specific T cells have antigen specificity to a virus.

9. The method of claim 8 wherein said virus is Epstein Barr Virus.

10. The method of claim 6 wherein said antigen presenting cells are lymphoblastoid cells.

11. The method of claim 6 wherein the method is a static cell culture method.

12. The method of claim 6 wherein said growth surface is gas permeable.

13. The method of claim 12 wherein the highest level of said media volume is beyond 2.0 cm from the lowest level of said media volume.

14. The method of claim 6 wherein the cell culture method is carried out in a G-Rex device.

* * * * *